US012369984B2

(12) United States Patent
VanDyken

(10) Patent No.: US 12,369,984 B2
(45) Date of Patent: Jul. 29, 2025

(54) SURGICAL SYSTEMS AND METHODS FOR PROVIDING SURGICAL GUIDANCE WITH A HEAD-MOUNTED DEVICE

(71) Applicant: Stryker Corporation, Kalamazoo, MI (US)

(72) Inventor: Benjamin VanDyken, Plainwell, MI (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/383,187

(22) Filed: Oct. 24, 2023

(65) Prior Publication Data

US 2024/0050156 A1 Feb. 15, 2024

Related U.S. Application Data

(63) Continuation of application No. 17/666,630, filed on Feb. 8, 2022, now Pat. No. 11,844,574, which is a
(Continued)

(51) Int. Cl.
*A61B 34/10* (2016.01)
*A61B 17/00* (2006.01)
(Continued)

(52) U.S. Cl.
CPC ............. *A61B 34/10* (2016.02); *A61B 34/20* (2016.02); *A61B 34/30* (2016.02); *A61B 90/37* (2016.02);
(Continued)

(58) Field of Classification Search
CPC ......... A61B 34/10; A61B 34/20; A61B 34/30; A61B 90/37; A61B 17/1675; A61B 34/32;
(Continued)

(56) References Cited

U.S. PATENT DOCUMENTS 5,682,886 A 11/1997 Delp et al.
5,766,016 A 6/1998 Sinclair et al.
(Continued)

FOREIGN PATENT DOCUMENTS

DE 10242953 3/2004
DE 10242953 A1 3/2004
(Continued)

OTHER PUBLICATIONS

English language abstract and machine-assisted English translation for DE 102 42 953 extracted from espacenet.com database on Mar. 27, 2019, 15 pages.
(Continued)

*Primary Examiner* — Jonathan T Kuo
(74) *Attorney, Agent, or Firm* — Howard & Howard Attorneys PLLC

(57) ABSTRACT

A head-mounted device (HMD) for use with a navigation system. The navigation system includes a localizer and a bone tracker coupled to a physical bone. The localizer monitors the bone tracker to track a pose of the physical bone in a localizer coordinate system. Controller(s) obtain surgical plan data related to the physical bone. The surgical plan data includes a virtual model of the physical bone and cut volume data defining material to be removed from the physical bone in preparation for receiving an implant. The controller(s) register the HMD to the localizer coordinate system and provide, on the HMD display, computer-generated imagery representative of the surgical plan data, including the virtual model of the physical bone and the cut volume data. The controller(s) align and combine the computer-generated imagery with a real-world view of the physical bone.

37 Claims, 9 Drawing Sheets

Related U.S. Application Data continuation of application No. 16/186,979, filed on Nov. 12, 2018, now Pat. No. 11,272,985.

(60) Provisional application No. 62/585,789, filed on Nov. 14, 2017.

(51) Int. Cl.

| | | |
|---|---|---|
| *A61B 17/16* | (2006.01) | |
| *A61B 34/00* | (2016.01) | |
| *A61B 34/20* | (2016.01) | |
| *A61B 34/30* | (2016.01) | |
| *A61B 34/32* | (2016.01) | |
| *A61B 90/00* | (2016.01) | |
| *G06T 19/00* | (2011.01) | |
| *G09B 9/00* | (2006.01) | |
| *G09B 23/28* | (2006.01) | |
| *G09B 23/30* | (2006.01) | |

(52) U.S. Cl.
CPC .......... *G06T 19/003* (2013.01); *G06T 19/006* (2013.01); *G09B 23/28* (2013.01); *G09B 23/30* (2013.01); *A61B 2017/00707* (2013.01); *A61B 17/1675* (2013.01); *A61B 2034/101* (2016.02); *A61B 2034/102* (2016.02); *A61B 2034/104* (2016.02); *A61B 2034/105* (2016.02); *A61B 2034/107* (2016.02); *A61B 2034/2055* (2016.02); *A61B 2034/252* (2016.02); *A61B 34/32* (2016.02); *A61B 34/76* (2016.02); *A61B 90/03* (2016.02); *A61B 2090/365* (2016.02); *G06T 2219/004* (2013.01); *G09B 9/00* (2013.01)

(58) Field of Classification Search
CPC .................. A61B 34/76; A61B 90/03; A61B 2017/00707; A61B 2034/101; A61B 2034/102; A61B 2034/104; A61B 2034/105; A61B 2034/107; A61B 2034/2055; A61B 2034/252; A61B 2090/365; G06T 19/003; G06T 19/006; G06T 2219/004; G09B 23/28; G09B 23/30; G09B 9/00

See application file for complete search history.

(56) References Cited

U.S. PATENT DOCUMENTS

| | | | |
|---|---|---|---|
| 5,800,177 A | 9/1998 | Gillio | |
| 6,544,041 B1 | 4/2003 | Damadian | |
| 6,711,432 B1 | 3/2004 | Krause et al. | |
| 7,121,832 B2 | 10/2006 | Hsieh et al. | |
| RE40,176 E | 3/2008 | Peshkin et al. | |
| 7,725,162 B2 | 5/2010 | Malackowski et al. | |
| 8,010,180 B2 | 8/2011 | Quaid et al. | |
| 8,500,451 B2 | 8/2013 | Bronstein et al. | |
| 8,560,047 B2 | 10/2013 | Haider et al. | |
| 8,675,939 B2 | 3/2014 | Moctezuma de la Barrera | |
| 9,119,655 B2 | 9/2015 | Bowling et al. | |
| 9,153,146 B2 | 10/2015 | Hyltander et al. | |
| 9,381,085 B2 | 7/2016 | Axelson, Jr. et al. | |
| 9,563,266 B2 | 2/2017 | Banerjee et al. | |
| 9,566,120 B2 | 2/2017 | Malackowski et al. | |
| 9,734,632 B2 | 8/2017 | Thomas et al. | |
| 9,788,905 B2 | 10/2017 | Avisar | |
| 9,839,486 B2 | 12/2017 | Hughes et al. | |
| 9,992,249 B2 | 6/2018 | Binns et al. | |
| 10,335,572 B1* | 7/2019 | Kumar .................. G06F 3/015 | |
| 11,272,985 B2 | 3/2022 | VanDyken | |
| 2004/0068187 A1 | 4/2004 | Krause et al. | |
| 2008/0077158 A1 | 3/2008 | Haider et al. | |
| 2011/0257653 A1 | 10/2011 | Hughes et al. | |
| 2011/0306986 A1 | 12/2011 | Lee et al. | |
| 2013/0063550 A1* | 3/2013 | Ritchey ............... A61B 5/7246 | |
| | | | 345/207 |
| 2013/0261433 A1 | 10/2013 | Daon | |
| 2015/0057675 A1 | 2/2015 | Akeel et al. | |
| 2015/0093734 A1 | 4/2015 | Kaouk | |
| 2015/0127316 A1 | 5/2015 | Avisar | |
| 2015/0185846 A1 | 7/2015 | Otto et al. | |
| 2017/0312032 A1* | 11/2017 | Amanatullah ......... G09B 23/30 | |
| 2018/0014891 A1* | 1/2018 | Krebs .................. A61B 8/0875 | |
| 2018/0049622 A1* | 2/2018 | Ryan .................... A61B 1/0005 | |
| 2018/0090029 A1 | 3/2018 | Fisher et al. | |
| 2018/0185100 A1 | 7/2018 | Weinstein et al. | |
| 2019/0005848 A1 | 1/2019 | Garcia Kilroy et al. | |
| 2019/0142520 A1 | 5/2019 | VanDyken | |
| 2022/0151703 A1 | 5/2022 | VanDyken | |

FOREIGN PATENT DOCUMENTS

| | | |
|---|---|---|
| EP | 1103229 | 5/2001 |
| EP | 1103229 A2 | 5/2001 |
| WO | 2016187399 A1 | 11/2016 |
| WO | WO2016187399 | 11/2016 |
| WO | 2016210081 A1 | 12/2016 |
| WO | WO2016210081 | 12/2016 |

OTHER PUBLICATIONS

Surgical Science, "LAP Mentor VR Webpage", https://simbionix.com/simulators/lap-mentor/lap-mentor-vr-or/, 2017, 2 pages.

* cited by examiner

SURGICAL SYSTEMS AND METHODS FOR PROVIDING SURGICAL GUIDANCE WITH A HEAD-MOUNTED DEVICE

CROSS-REFERENCE TO RELATED APPLICATIONS

The subject application is a continuation of U.S. patent application Ser. No. 17/666,630, filed on Feb. 8, 2022, which is a continuation of U.S. patent application Ser. No. 16/186,979, filed on Nov. 12, 2018, now U.S. Pat. No. 11,272,985, which claims the benefit of and priority to U.S. Provisional Patent App. No. 62/585,789, filed Nov. 14, 2017, the disclosure of each of the aforementioned applications being hereby incorporated by reference in their respective entirety.

TECHNICAL FIELD

The disclosure relates generally to surgical systems and methods for providing surgical guidance.

BACKGROUND

Surgical navigation systems assist users in locating objects in one or more coordinate systems. Surgical navigation systems may employ light signals, sound waves, magnetic fields, radio frequency signals, etc. in order to track positions and/or orientations of the objects. Often the surgical navigation system includes tracking devices attached to the objects being tracked. A surgical navigation localizer cooperates with the tracking devices to ultimately determine positions and/or orientations of the objects. The surgical navigation system monitors movement of the objects via the tracking devices.

Surgeries in which surgical navigation systems are used include neurosurgery and orthopedic surgery, among others. Typically, surgical tools and anatomy being treated are tracked together in real-time in a common coordinate system with their relative positions and/or orientations shown on a display. In some cases, this visualization may include computer-generated images of the surgical tools and/or the anatomy displayed in conjunction with real video images of the surgical tools and/or the anatomy to provide mixed reality visualization. This visualization assists surgeons in performing the surgery.

Even with the assistance of such surgical navigation systems, surgeons may still encounter difficulty in performing surgical procedures. This is especially true where surgeons are called to perform unfamiliar procedures or procedures that they have not performed recently.

SUMMARY

According to a first aspect, a surgical system is provided, comprising: a head-mounted device (HMD) comprising an HMD controller and a display that is configured to be located in front of eyes of a wearer of the HMD; a navigation system comprising a localizer and a bone tracker coupled to a physical bone of a patient, wherein the localizer comprises a localizer coordinate system and is configured to monitor the bone tracker to track a pose of the physical bone in the localizer coordinate system, wherein the navigation system is configured to: obtain surgical plan data related to the physical bone, wherein the surgical plan data comprises a virtual model of the physical bone and cut volume data defining material to be removed from the physical bone in preparation for receiving an implant; register the HMD to the localizer coordinate system using the localizer such that the localizer is able to obtain a pose of the HMD; and transmit the surgical plan data to the HMD controller; and wherein the HMD controller is configured to: provide, on the display, computer-generated imagery representative of the surgical plan data, including the virtual model of the physical bone and the cut volume data; and align and combine the computer-generated imagery with a real-world view of the physical bone.

According to a second aspect, a method of operating a surgical system is provided, the surgical system comprising a head-mounted device (HMD) including an HMD controller and a display that is configured to be located in front of eyes of a wearer of the HMD, a navigation system including a localizer and a bone tracker coupled to a physical bone of a patient, wherein the localizer comprises a localizer coordinate system and is configured to monitor the bone tracker to track a pose of the physical bone in the localizer coordinate system, the method comprising: with the navigation system: obtaining surgical plan data related to the physical bone, wherein the surgical plan data comprises a virtual model of the physical bone and cut volume data defining material to be removed from the physical bone in preparation for receiving an implant; registering the HMD to the localizer coordinate system using the localizer such that the localizer is able to obtain a pose of the HMD; and transmitting the surgical plan data to the HMD controller; and with the HMD controller: providing, on the display, computer-generated imagery representative of the surgical plan data, including the virtual model of the physical bone and the cut volume data; and aligning and combining the computer-generated imagery with a real-world view of the physical bone.

According to a third aspect, a head-mounted device (HMD) is provided for use with a navigation system, the navigation system including a localizer and a bone tracker coupled to a physical bone of a patient, wherein the localizer comprises a localizer coordinate system and is configured to monitor the bone tracker to track a pose of the physical bone in the localizer coordinate system, the HMD comprising: an HMD controller; and a display that is configured to be located in front of eyes of a wearer of the HMD; and wherein the HMD controller is configured to: receive, from the navigation system, surgical plan data related to the physical bone, wherein the surgical plan data comprises a virtual model of the physical bone and cut volume data defining material to be removed from the physical bone in preparation for receiving an implant; register to the localizer coordinate system; provide, on the display, computer-generated imagery representative of the surgical plan data, including the virtual model of the physical bone and the cut volume data; and align and combine the computer-generated imagery with a real-world view of the physical bone.

According to a fourth aspect, a head-mounted device (HMD) is provided for providing surgical guidance related to a physical bone of a patient, the HMD comprising: an HMD controller; a video camera; and a display that is configured to be located in front of eyes of a wearer of the HMD; and wherein the HMD controller is configured to: receive surgical plan data related to the physical bone, wherein the surgical plan data comprises a virtual model of the physical bone and cut volume data defining material to be removed from the physical bone in preparation for receiving an implant; register to the physical bone; provide, on the display, computer-generated imagery representative of the surgical plan data, including the virtual model of the physical bone and the cut volume data; and align and combine the computer-generated imagery with a real-world video of the physical bone captured by the video camera.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

I. System Overview

Figure 1:
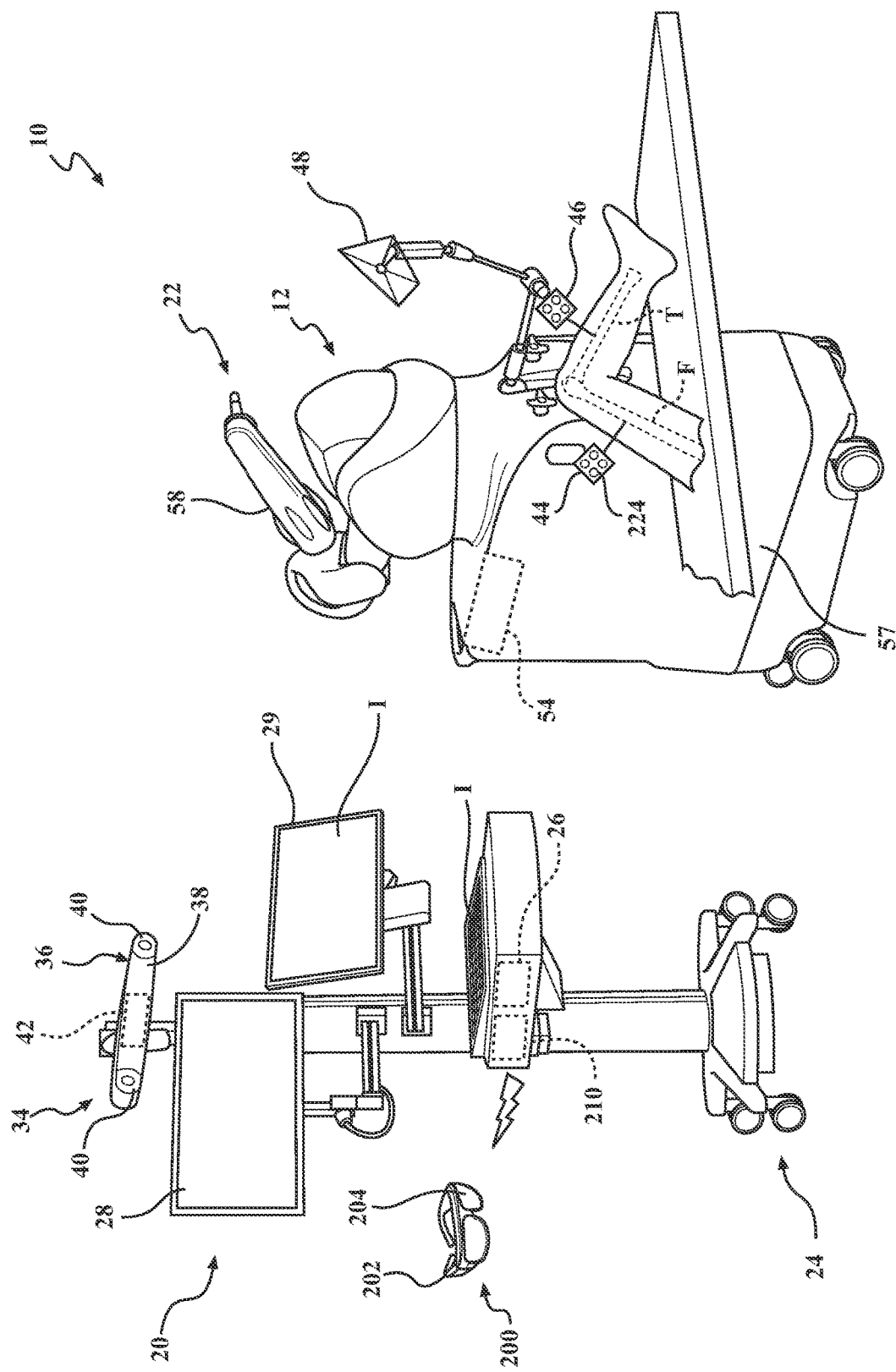
FIG. 1 is a perspective view of a robotic system.

In the embodiments disclosed herein, a surgical system is described that includes a navigation system and a robotic manipulator to which a surgical tool is removably attached. Alternatively, the system may not include the robotic manipulator such that the surgical tool is a handheld tool usable by a surgeon. At least some portions of the surgical system may be used to preoperatively simulate a surgical procedure before the procedure is performed intraoperatively. The simulation may use one or more physical tools, such as the tool attached to the manipulator. Alternatively, the simulation may use one or more virtual tools that are displayed by a display.

As used herein, the term "simulation" refers to the preoperative performance of the steps of a surgical workflow corresponding to an intraoperative performance of a surgical procedure. The simulation allows a surgeon to practice the procedure before the procedure actually takes place on a real patient. Accordingly, at least some of the steps of the simulation directly correspond to the steps of the intraoperative procedure in some embodiments. As described more fully herein, the surgeon may adjust a pose of the tool to interact with the preoperative model of the patient anatomy during the simulation. For example, the surgeon may move the tool into contact with the model of the anatomy and may use the tool to cut away portions of the model of the anatomy or otherwise interact with the model of the anatomy during the simulation. The simulation of the surgical procedure may involve the use of the same tool (or the same type of tool) as will be used in the actual intraoperative procedure, or may involve the use of a virtual representation of the physical tool that will be used in the actual procedure.

As used herein, the term "movement" of a tool or other object refers to a change in pose of the tool or object over time. The pose of the tool or object includes the position and/or orientation of the tool or object. Accordingly, the tracking of a tool may include tracking the pose (i.e., the position and/or orientation) of the tool in addition to tracking other parameters of the tool.

In embodiments in which a physical tool is used during the simulation of the surgical procedure, a surgeon may operate the physical tool to perform the steps of the surgical workflow on a mannequin, a physical model of the patient's anatomy (e.g., a cast mold or model of the patient's anatomy), or the like. Accordingly, as used herein, the term "physical tool" refers to a surgical tool or other physical tool simulating operation of a surgical tool that may be physically handled by the surgeon to interact with the patient's anatomy or to interact with a physical model or mold of an anatomy. For example, in one embodiment, the physical tool may be a handheld wand or other device that is tracked by a camera or other tracking sensor. The tool may include an integrated infrared or other marker that may cooperate with the tracking sensor to track the pose of the tool over time. When viewed using a head mounted display (HMD) or the like, a virtual graphical representation of the surgical tool may be displayed to the user by the HMD. Alternatively, the physical tool may be physically handled by the surgeon to perform a simulation using a virtual model of an anatomy as described herein.

In embodiments in which a virtual tool is used during the simulation of the surgical procedure, the surgeon may provide inputs into a computer to operate the virtual tool to perform the steps of the surgical workflow on patient image data, such as a two-dimensional image of the patient's anatomy or a three-dimensional image or model of the patient's anatomy. Accordingly, as used herein, the term "virtual tool" refers to a graphical model or image of a surgical tool that is displayed within a display device and that may be virtually moved as a result of a surgeon manipulating an input device such as a mouse, keyboard, touch sensitive screen, gesture input via computer vision, wand or other device that is tracked by a camera or other tracking device, or the like. The virtual tool may be visually displayed as interacting with a virtual model of the patient's anatomy in some embodiments.

During the simulation of the surgical procedure using a physical tool, a physical or virtual model of the patient's anatomy is provided. The navigation system tracks the pose of the tool in relation to the model of the patient's anatomy using a plurality of trackers. As the surgeon performs the steps of the surgical workflow associated with the surgical procedure using the physical tool, a surgical planning program generates one or more planning parameters to be included within a surgical plan. The planning parameters and the surgical plan are stored within the surgical planning program when the simulation has completed.

During the simulation of the surgical procedure using a virtual tool, patient image data is displayed on a display. The patient image data may be preoperatively obtained using MRI, CT, PET, fluoroscopy, and/or any other imaging modality. As noted above, the patient image data may be displayed as one or more two-dimensional images of the patient's anatomy, or may be displayed as a three-dimensional model of the patient's anatomy. A virtual representation of the tool is also displayed on the display in relation to the patient image data. As the surgeon performs the steps of the surgical workflow associated with the surgical procedure using the virtual tool, the surgical planning program generates one or more planning parameters to be included within the surgical plan. The planning parameters and the surgical plan are stored within the surgical planning program when the simulation has completed.

In some embodiments, preoperative simulation may involve a combination of both physical and virtual techniques. For instance, a physical tool may be used during the simulation and a computer display, such as augmented reality eyewear, may project patient image data onto the patient model as the physical tool interacts with the patient model.

After the simulation has completed, the surgeon may perform the surgical procedure intraoperatively on the actual patient using a physical tool. The planning parameters and the surgical plan are loaded from the surgical planning program. The tool, the patient's anatomy, and one or more of the planning parameters can be registered by the navigation system and are transformed into the coordinate system of the navigation system. The planning parameters may then be displayed to the surgeon while the surgeon executes the surgical procedure.

The above embodiment is described with the surgeon performing the intraoperative surgical procedure (by either manually operating the surgical tool or operating the surgical tool semi-autonomously with assistance from the manipulator). However, in an alternative embodiment, the manipulator may autonomously perform the surgical procedure by autonomously operating the surgical tool. In such an embodiment, the manipulator may load the planning parameters into memory and a manipulator controller may automatically cause the manipulator to follow the planning parameters. For example, in an embodiment in which a planning parameter identifies a path for the surgical tool to follow, the manipulator controller may autonomously control the movement of the surgical tool to follow the tool path identified in the planning parameter.

Accordingly, the embodiments described herein provide an improved surgical experience to surgeons or other health care professionals involved in the surgical procedure. The simulation of the surgical procedure enables the surgeon to trial a variety of approaches to performing the surgical workflow associated with the surgical procedure without fear of harming the patient. The simulation program can intelligently identify behavior and/or actions relating to the tool during the simulation for automatically generating parameters or plans for intraoperative surgery. The surgeon may then use the parameters or surgical plan generated as a result of the simulation and may view the parameters intraoperatively while performing the actual surgical procedure. As a result, the surgeon may reduce a number of errors during the actual surgery and may realize an increased level of confidence in performing the actual surgical procedure using the embodiments described herein.

Referring to FIG. 1, a surgical system 10 for treating a patient is illustrated. The surgical system 10 is shown in a surgical setting such as an operating room of a medical facility. As shown in FIG. 1, the surgical system 10 may be used to perform an intraoperative surgical procedure on a patient. In addition, the surgical system 10, or portions thereof, may be used to perform a preoperative simulation of the surgical procedure as described more fully herein.

In the embodiment shown, the surgical system 10 includes a manipulator 12 and a navigation system 20. The navigation system 20 is set up to track movement of various objects in the operating room. Such objects include, for example, a surgical tool 22, a femur F of a patient, and a tibia T of the patient. The navigation system 20 tracks these objects for purposes of displaying their relative positions and orientations to the surgeon and, in some cases, for purposes of controlling or constraining movement of the surgical tool 22 relative to virtual cutting boundaries (not shown) associated with the femur F and tibia T. An example control scheme for the surgical system 10 is shown in FIG. 2.

Figure 2:
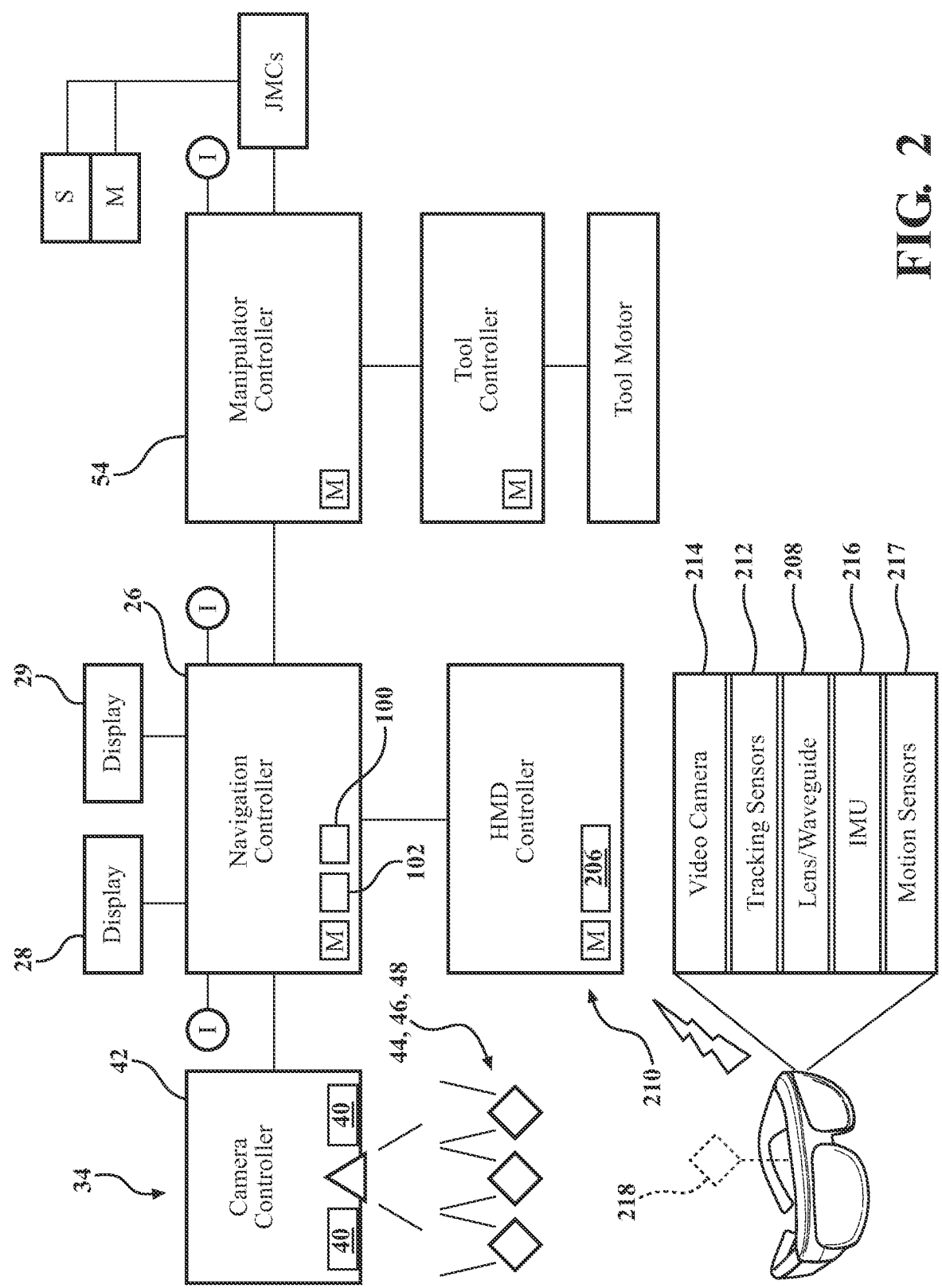
FIG. 2 is a schematic view of a control system.
Figure 3:
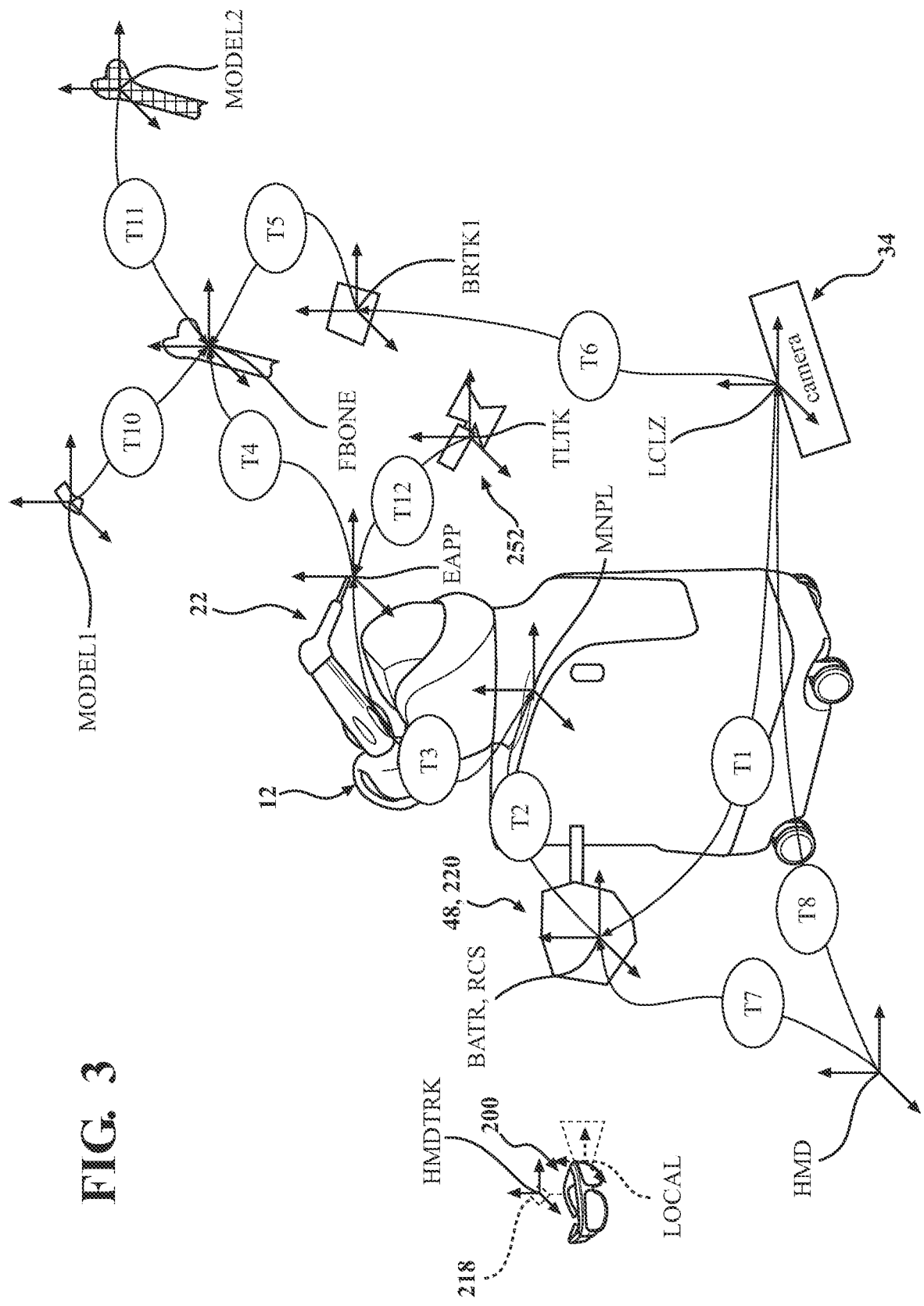
FIG. 3 is an illustration of various transforms used in navigation.

While the surgical system 10 is illustrated in FIGS. 1-3 as including a surgical robot (i.e., manipulator 12) that includes a surgical tool 22 attached to an end of the manipulator 12, it should be recognized that the surgical system 10 may include one or more manually-operated surgical tools 22 instead. For example, the surgical tool 22 may include a hand-held motorized saw, reamer, bur, or other suitable tool that may be held and manually operated by a surgeon. The following embodiments will be described with reference to the use of the manipulator 12 with the understanding that the embodiments may also apply to the use of a manually-operated tool 22 with appropriate modifications. In addition, the following embodiments describe the use of the surgical system 10 in performing a procedure in which material is removed from a femur F and/or a tibia T of a patient. However, it should be recognized that the surgical system 10 may be used to perform any suitable procedure in which material is removed from any suitable portion of a patient's anatomy (e.g., an osteotomy), material is added to any suitable portion of the patient's anatomy (e.g., an implant, graft, etc.), and/or in which any other control over a surgical tool is desired.

The navigation system 20 includes one or more computer cart assemblies 24 that houses one or more navigation controllers 26. A navigation interface is in operative communication with the navigation controller 26. The navigation interface includes one or more displays 28, 29 adjustably mounted to the computer cart assembly 24 or mounted to separate carts as shown. Input devices I such as a keyboard and mouse can be used to input information into the navigation controller 26 or otherwise select/control certain aspects of the navigation controller 26. Other input devices I are contemplated including a touch screen, a microphone for voice-activation input, an optical sensor for gesture input, and the like.

A surgical navigation localizer 34 communicates with the navigation controller 26. In the embodiment shown, the localizer 34 is an optical localizer and includes a camera unit 36. In other embodiments, the localizer 34 employs other modalities for tracking, e.g., radio frequency (RF), ultrasonic, electromagnetic, inertial, and the like. The camera unit 36 has a housing 38 comprising an outer casing that houses one or more optical position sensors 40. In some embodiments at least two optical sensors 40 are employed, preferably three or four. The optical sensors 40 may be separate charge-coupled devices (CCD). In one embodiment three, one-dimensional CCDs are employed. Two-dimensional or three-dimensional sensors could also be employed. It should be appreciated that in other embodiments, separate camera units, each with a separate CCD, or two or more CCDs, could also be arranged around the operating room. The CCDs detect light signals, such as infrared (IR) signals.

Camera unit 36 is mounted on an adjustable arm to position the optical sensors 40 with a field-of-view of the below discussed trackers that, ideally, is free from obstructions. In some embodiments the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 communicates with the navigation controller 26 through either a wired or wireless connection (not shown). One such connection may be an IEEE 1394 interface. Additionally or alternatively, the connection may use a company-specific protocol. In other embodiments, the optical sensors 40 communicate directly with the navigation controller 26.

Position and orientation signals and/or data are transmitted to the navigation controller 26 for purposes of tracking objects. The computer cart assembly 24, display 28, and camera unit 36 may be like those described in U.S. Pat. No. 7,725,162 to Malackowski, et al. issued on May 25, 2010, entitled "Surgery System," the disclosure of which is hereby incorporated by reference.

The navigation controller 26 can be a personal computer or laptop computer. Navigation controller 26 includes the displays 28, 29, central processing unit (CPU) and/or other processors, memory (not shown), and storage (not shown). The navigation controller 26 is loaded with software as described below. The software converts the signals received from the camera unit 36 into data representative of the position and orientation of the objects being tracked.

Navigation system 20 is operable with a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone in an embodiment. For example, trackers 44, 46 may be attached to the femur F and tibia T in the manner shown in U.S. Pat. No. 7,725,162 to Malackowski, et al. issued on May 25, 2010, entitled "Surgery System," the disclosure of which is hereby incorporated by reference. Trackers 44, 46 may also be mounted like those shown in U.S. patent application Ser. No. 14/156,856, filed on Jan. 16, 2014, entitled, "Navigation Systems and Methods for Indicating and Reducing Line-of-Sight Errors," hereby incorporated by reference herein. In additional embodiments, a tracker (not shown) may be attached to the patella to track a position and orientation of the patella. In yet further embodiments, the trackers 44, 46 may be mounted to other tissue types or parts of the anatomy.

A tool tracker 48 is shown coupled to the manipulator 12. In other embodiments, a base tracker (not shown) may be substituted for the tool tracker 48, for example, in embodiments in which a hand-held tool 22 is used. The tool tracker 48 may be integrated into the surgical tool 22 during manufacture or may be separately mounted to the surgical tool 22 (or to an end effector attached to the manipulator 12 of which the surgical tool 22 forms a part) in preparation for surgical procedures. The working end of the surgical tool 22, which is being tracked by virtue of the tool tracker 48, may be referred to herein as an energy applicator, and may be a rotating bur, electrical ablation device, probe, or the like.

In the embodiment shown, the surgical tool 22 is attached to the manipulator 12. Such an arrangement is shown in U.S. Pat. No. 9,119,655, entitled, "Surgical Manipulator Capable of Controlling a Surgical Instrument in Multiple Modes," the disclosure of which is hereby incorporated by reference.

The optical sensors 40 of the localizer 34 receive light signals from the trackers 44, 46, 48. In the illustrated embodiment, the trackers 44, 46, 48 are passive trackers. In this embodiment, each tracker 44, 46, 48 has at least three passive tracking elements or markers (e.g., reflectors) for transmitting light signals (e.g., reflecting light emitted from the camera unit 36) to the optical sensors 40. In other embodiments, active tracking markers can be employed. The active markers can be, for example, light emitting diodes transmitting light, such as infrared light. Active and passive arrangements are possible.

The navigation controller 26 includes a navigation processor. It should be understood that the navigation processor could include one or more processors to control operation of the navigation controller 26. The processors can be any type of microprocessor or multi-processor system. The term processor is not intended to limit the scope of any embodiment to a single processor.

The camera unit 36 receives optical signals from the trackers 44, 46, 48 and outputs to the navigation controller 26 signals relating to the position of the tracking markers of the trackers 44, 46, 48 relative to the localizer 34. Based on the received optical signals, navigation controller 26 generates data indicating the relative positions and orientations of the trackers 44, 46, 48 relative to the localizer 34. In one version, the navigation controller 26 uses well known triangulation methods for determining position data.

Prior to the start of the surgical procedure, additional data are loaded into the navigation controller 26. Based on the position and orientation of the trackers 44, 46, 48 and the previously loaded data, navigation controller 26 determines the position of the working end of the surgical tool 22 (e.g., the centroid of a surgical bur) and/or the orientation of the surgical tool 22 relative to the tissue against which the working end is to be applied. In some embodiments, the navigation controller 26 forwards these data to a manipulator controller 54. The manipulator controller 54 can then use the data to control the manipulator 12. This control can be like that described in U.S. Pat. No. 9,119,655, entitled, "Surgical Manipulator Capable of Controlling a Surgical Instrument in Multiple Modes," or like that described in U.S. Pat. No. 8,010,180, entitled, "Haptic Guidance System and Method", the disclosures of which are hereby incorporated by reference.

In one embodiment, the manipulator 12 is controlled to stay within a preoperatively defined virtual boundary (sometimes referred to as a stereotactic boundary) set by the surgeon or others (not shown). The virtual or stereotactic boundary may be a virtual cutting boundary which defines the material of the anatomy (e.g., the femur F and tibia T) to be removed by the surgical tool 22. More specifically, each of the femur F and tibia T has a target volume of material that is to be removed by the working end of the surgical tool 22. The target volumes are defined by one or more virtual cutting boundaries. The virtual cutting boundaries define the surfaces of the bone that should remain after the procedure. The navigation system 20 tracks and controls the surgical tool 22 to ensure that the working end, e.g., the surgical bur, only removes the target volume of material and does not extend beyond the virtual cutting boundary, as disclosed in U.S. Pat. No. 9,119,655, entitled, "Surgical Manipulator Capable of Controlling a Surgical Instrument in Multiple Modes," the disclosure of which is hereby incorporated by reference, or as disclosed in U.S. Pat. No. 8,010,180, entitled, "Haptic Guidance System and Method", the disclosure of which is hereby incorporated by reference.

The virtual cutting boundary may be defined within a virtual model of the anatomy (e.g., the femur F and tibia T), or separately from the virtual model. The virtual cutting boundary may be represented as a mesh surface, constructive solid geometry (CSG), voxels, or using other boundary representation techniques. The surgical tool 22 may be used to cut away material from the femur F and tibia T to receive an implant. The surgical implants may include unicompartmental, bicompartmental, or total knee implants as shown in U.S. Pat. No. 9,381,085, entitled, "Prosthetic Implant and Method of Implantation," the disclosure of which is hereby incorporated by reference. Other implants, such as hip implants, shoulder implants, spine implants, and the like are also contemplated. The focus of the description on knee implants is provided as one example. These concepts can be equally applied to other types of surgical procedures, including those performed without placing implants.

The navigation controller 26 also generates image signals that indicate the relative position of the working end to the tissue. These image signals are applied to the displays 28, 29. The displays 28, 29, based on these signals, generate images that allow the surgeon and staff to view the relative position of the working end to the surgical site. The displays, 28, 29, as discussed above, may include a touch screen or other input/output device that allows entry of commands.

Referring to FIG. 3, tracking of objects is generally conducted with reference to a localizer coordinate system LCLZ. The localizer coordinate system has an origin and an orientation (a set of x, y, and z axes). During the procedure one goal is to keep the localizer coordinate system LCLZ in a known position. An accelerometer (not shown) mounted to the localizer 34 may be used to track sudden or unexpected movement of the localizer coordinate system LCLZ, as may occur when the localizer 34 is inadvertently bumped by surgical personnel.

Each tracker 44, 46, 48 and object being tracked also has its own coordinate system separate from the localizer coordinate system LCLZ. Components of the navigation system 20 that have their own coordinate systems are the bone trackers 44, 46 (only one of which is shown in FIG. 3) and the base tracker 48. These coordinate systems are represented as, respectively, bone tracker coordinate systems BTRK1, BTRK2 (only BTRK1 shown), and base tracker coordinate system BATR.

Navigation system 20 monitors the positions of the femur F and tibia T of the patient by monitoring the position of bone trackers 44, 46 firmly attached to bone. Femur coordinate system is FBONE and tibia coordinate system is TBONE, which are the coordinate systems of the bones to which the bone trackers 44, 46 are firmly attached.

Prior to the start of the intraoperative procedure, preoperative images of the femur F and tibia T are generated (or of other portions of the anatomy in other embodiments). The preoperative images are stored as two-dimensional or three-dimensional patient image data in a computer-readable storage device, such as memory within the navigation system 20. The patient image data may be based on MRI scans, radiological scans or computed tomography (CT) scans of the patient's anatomy. The patient image data may then be used to generate two-dimensional images or three-dimensional models of the patient's anatomy. A simulation of the procedure may then be performed, for example, as described more fully herein with reference to FIGS. 5A-B or FIG. 6.

In preparation for the intraoperative procedure, the images or three-dimensional models developed from the image data are mapped to the femur coordinate system FBONE and tibia coordinate system TBONE (see transform T11). One of these models is shown in FIG. 3 with model coordinate system MODEL2. These images/models are fixed in the femur coordinate system FBONE and tibia coordinate system TBONE. As an alternative to taking preoperative images, plans for treatment can be developed in the operating room (OR) from kinematic studies, bone tracing, and other methods. The models described herein may be represented by mesh surfaces, constructive solid geometry (CSG), voxels, or using other model constructs.

During an initial phase of the intraoperative procedure, the bone trackers 44, 46 are coupled to the bones of the patient. The pose (position and orientation) of coordinate systems FBONE and TBONE are mapped to coordinate systems BTRK1 and BTRK2, respectively (see transform T5). In one embodiment, a pointer instrument 252 (TLTK), such as disclosed in U.S. Pat. No. 7,725,162 to Malackowski, et al., hereby incorporated by reference, having its own tracker, may be used to register the femur coordinate system FBONE and tibia coordinate system TB ONE to the bone tracker coordinate systems BTRK1 and BTRK2, respectively. Given the fixed relationship between the bones and their bone trackers 44, 46, positions and orientations of the femur F and tibia T in the femur coordinate system FBONE and tibia coordinate system TB ONE can be transformed to the bone tracker coordinate systems BTRK1 and BTRK2 so the camera unit 36 is able to track the femur F and tibia T by tracking the bone trackers 44, 46. These pose-describing data are stored in memory integral with both manipulator controller 54 and navigation controller 26.

The working end of the surgical tool 22 has its own coordinate system. In some embodiments, the surgical tool 22 comprises a handpiece and an accessory that is removably coupled to the handpiece. The accessory may be referred to as the energy applicator and may comprise a bur, an electrosurgical tip, an ultrasonic tip, or the like. Thus, the working end of the surgical tool 22 may comprise the energy applicator. The coordinate system of the surgical tool 22 is referenced herein as coordinate system EAPP. The origin of the coordinate system EAPP may represent a centroid of a surgical cutting bur, for example. In other embodiments, the accessory may simply comprise a probe or other surgical tool with the origin of the coordinate system EAPP being a tip of the probe. The pose of coordinate system EAPP is registered to the pose of base tracker coordinate system BATR before the procedure begins (see transforms T1, T2, T3). Accordingly, the poses of these coordinate systems EAPP, BATR relative to each other are determined. The pose-describing data are stored in memory integral with both manipulator controller 54 and navigation controller 26.

Referring to FIG. 2, a localization engine 100 is a software module that can be considered part of the navigation system 20. Components of the localization engine 100 run on navigation controller 26. In some embodiments, the localization engine 100 may run on the manipulator controller 54.

Localization engine 100 receives as inputs the optically-based signals from the camera controller 42 and, in some embodiments, non-optically based signals from the tracker controller. Based on these signals, localization engine 100 determines the pose of the bone tracker coordinate systems BTRK1 and BTRK2 in the localizer coordinate system LCLZ (see transform T6). Based on the same signals received for the base tracker 48, the localization engine 100 determines the pose of the base tracker coordinate system BATR in the localizer coordinate system LCLZ (see transform T1).

The localization engine 100 forwards the signals representative of the poses of trackers 44, 46, 48 to a coordinate transformer 102. Coordinate transformer 102 is a navigation system software module that runs on navigation controller 26. Coordinate transformer 102 references the data that defines the relationship between the preoperative images of the patient and the bone trackers 44, 46. Coordinate transformer 102 also stores the data indicating the pose of the working end of the surgical tool 22 relative to the base tracker 48.

During the procedure, the coordinate transformer 102 receives the data indicating the relative poses of the trackers 44, 46, 48 to the localizer 34. Based on these data, the previously loaded data, and the below-described encoder data from the manipulator 12, the coordinate transformer 102 generates data indicating the relative positions and orientations of the coordinate system EAPP and the bone coordinate systems, FBONE and TB ONE.

As a result, coordinate transformer 102 generates data indicating the position and orientation of the working end of the surgical tool 22 relative to the tissue (e.g., bone) against which the working end is applied Image signals representative of these data are forwarded to displays 28, 29 enabling the surgeon and staff to view this information. In certain embodiments, other signals representative of these data can be forwarded to the manipulator controller 54 to guide the manipulator 12 and corresponding movement of the surgical tool 22.

In this example, the surgical tool 22 forms part of the end effector of the manipulator 12. The manipulator 12 has a base 57, a plurality of links 58 extending from the base 57, and a plurality of active joints (not numbered) for moving the surgical tool 22 with respect to the base 57. The manipulator 12 has the ability to operate in a manual mode or a semi-autonomous mode in which the surgical tool 22 is moved along a predefined tool path, as described in U.S. Pat. No. 9,119,655, entitled, "Surgical Manipulator Capable of Controlling a Surgical Instrument in Multiple Modes," the disclosure of which is hereby incorporated by reference, or the manipulator 12 may be configured to move in the manner described in U.S. Pat. No. 8,010,180, entitled, "Haptic Guidance System and Method", the disclosure of which is hereby incorporated by reference.

The manipulator controller 54 can use the position and orientation data of the surgical tool 22 and the patient's anatomy to control the manipulator 12 as described in U.S. Pat. No. 9,119,655, entitled, "Surgical Manipulator Capable of Controlling a Surgical Instrument in Multiple Modes," the disclosure of which is hereby incorporated by reference, or to control the manipulator 12 as described in U.S. Pat. No. 8,010,180, entitled, "Haptic Guidance System and Method", the disclosure of which is hereby incorporated by reference.

The manipulator controller 54 may have a central processing unit (CPU) and/or other manipulator processors, memory (not shown), and storage (not shown). The manipulator controller 54, also referred to as a manipulator computer, is loaded with software as described below. The manipulator processors could include one or more processors to control operation of the manipulator 12. The processors can be any type of microprocessor or multi-processor system. The term processor is not intended to limit any embodiment to a single processor.

A plurality of position sensors S are associated with the plurality of links 58 of the manipulator 12. In one embodiment, the position sensors S are encoders. The position sensors S may be any suitable type of encoder, such as rotary encoders. Each position sensor S is associated with a joint actuator, such as a joint motor M. Each position sensor S is a sensor that monitors the angular position of one of six motor driven links 58 of the manipulator 12 with which the position sensor S is associated. Multiple position sensors S may be associated with each joint of the manipulator 12 in some embodiments. The manipulator 12 may be in the form of a conventional robot or other conventional machining apparatus, and thus the components thereof shall not be described in detail.

In some modes, the manipulator controller 54 determines the desired location to which the surgical tool 22 should be moved. Based on this determination, and information relating to the current location (e.g., pose) of the surgical tool 22, the manipulator controller 54 determines the extent to which each of the plurality of links 58 needs to be moved in order to reposition the surgical tool 22 from the current location to the desired location. The data regarding where the plurality of links 58 are to be positioned is forwarded to joint motor controllers JMCs that control the joints of the manipulator 12 to move the plurality of links 58 and thereby move the surgical tool 22 from the current location to the desired location. In other modes, the manipulator 12 is capable of being manipulated as described in U.S. Pat. No. 8,010,180, entitled, "Haptic Guidance System and Method", the disclosure of which is hereby incorporated by reference, in which case the actuators are controlled by the manipulator controller 54 to provide gravity compensation to prevent the surgical tool 22 from lowering due to gravity and/or to activate in response to a user attempting to place the working end of the surgical tool 22 beyond a virtual boundary.

In order to determine the current location of the surgical tool 22, data from the position sensors S is used to determine measured joint angles. The measured joint angles of the joints are forwarded to a forward kinematics module, as known in the art. Based on the measured joint angles and preloaded data, the forward kinematics module determines the pose of the surgical tool 22 in a manipulator coordinate system MNPL (see transform T3 in FIG. 3). The preloaded data are data that define the geometry of the plurality of links 58 and joints. With this encoder-based data, the manipulator controller 54 and/or navigation controller 26 can transform coordinates from the localizer coordinate system LCLZ into the manipulator coordinate system MNPL, vice versa, or can transform coordinates from one coordinate system into any other coordinate system described herein using conventional transformation techniques. In many cases, the coordinates of interest associated with the surgical tool 22 (e.g., the tool center point or TCP), the virtual boundaries, and the tissue being treated, are transformed into a common coordinate system for purposes of relative tracking and display.

In the embodiment shown in FIG. 3, transforms T1-T6 are utilized to transform all relevant coordinates into the femur coordinate system FBONE so that the position and/or orientation of the surgical tool 22 can be tracked relative to the position and orientation of the femur (e.g., the femur model) and/or the position and orientation of the volume of material to be treated by the surgical tool 22 (e.g., a cut-volume model: see transform T10). The relative positions and/or orientations of these objects can also be represented on the displays 28, 29 to enhance the user's visualization before, during, and/or after surgery.

Referring back to FIGS. 1 and 2, a head-mounted display (HMD) 200 may be employed to enhance visualization before, during, and/or after surgery. The HMD 200 can be used to visualize the same objects previously described as being visualized on the displays 28, 29, and can also be used to visualize other objects, features, instructions, warnings, etc. The HMD 200 can be used to assist with visualization of the volume of material to be cut from the patient, to help visualize the size of implants and/or to place implants for the patient, to assist with registration and calibration of objects being tracked via the navigation system 20, to see instructions and/or warnings, among other uses, as described further below.

The HMD 200 may be a mixed reality HMD that overlays computer-generated images onto objects viewed in the real world. Thus, in the embodiment described herein, the HMD provides a computational holographic display. Other types of mixed reality HMDs may also be used such as those that overlay computer-generated images onto video images of the real world. In other embodiments, the HMD 200 may include an augmented reality device, a virtual reality device, or a holographic projection device. The HMD 200 may comprise a cathode ray tube display, liquid crystal display, liquid crystal on silicon display, or organic light-emitting diode display. The HMD 200 may comprise see-through techniques like that described herein comprising a diffractive waveguide, holographic waveguide, polarized waveguide, reflective waveguide, or switchable waveguide.

The HMD 200 includes a head-mountable structure 202, which may be in the form of an eyeglass and may include additional headbands or supports to hold the HMD 200 on the user's head. In other embodiments, the HMD 200 may be integrated into a helmet or other structure worn on the user's head, neck, and/or shoulders.

The HMD 200 has visor 204 and a lens/waveguide arrangement 208. The lens/waveguide arrangement 208 is configured to be located in front of the user's eyes when the HMD is placed on the user's head. The waveguide transmits the computer-generated images to the user's eyes while at the same time, real images are seen through the waveguide (it being transparent) such that the user sees mixed reality (virtual and real).

An HMD controller 210 comprises an image generator 206 that generates the computer-generated images (also referred to as virtual images) and that transmits those images to the user through the lens/waveguide arrangement 208. The HMD controller 210 controls the transmission of the computer-generated images to the lens/waveguide arrangement 208 of the HMD 200. The HMD controller 210 may be a separate computer, located remotely from the support structure 202 of the HMD 200, or may be integrated into the support structure 202 of the HMD 200. The HMD controller 210 may be a laptop computer, desktop computer, microcontroller, or the like with memory, one or more processors (e.g., multi-core processors), input devices I, output devices (fixed display in addition to HMD 200), storage capability, etc.

The HMD 200 comprises a plurality of tracking sensors 212 that are in communication with the HMD controller 210. In some cases, the tracking sensors 212 are provided to establish a global coordinate system for the HMD 200, also referred to as an HMD coordinate system. The HMD coordinate system is established by these tracking sensors 212, which may comprise CMOS sensors or other sensor types, in some cases combined with IR depth sensors, to layout the space surrounding the HMD 200, such as using structure-from-motion techniques or the like. In one embodiment, four tracking sensors 212 are employed.

The HMD 200 also comprises a photo/video camera 214 in communication with the HMD controller 210. The camera 214 may be used to obtain photographic or video images 214 with the HMD 200, which can be useful in identifying objects or markers attached to objects, as will be described further below.

The HMD 200 further comprises an inertial measurement unit IMU 216 in communication with the HMD controller 210. The IMU 216 may comprise one or more 3-D accelerometers, 3-D gyroscopes, and the like to assist with determining a position and/or orientation of the HMD 200 in the HMD coordinate system or to assist with tracking relative to other coordinate systems. The HMD 200 may also comprise an infrared motion sensor 217 to recognize gesture commands from the user. Other types of gesture sensors are also contemplated. The motion sensor 217 may be arranged to project infrared light or other light in front of the HMD 200 so that the motion sensor 217 is able to sense the user's hands, fingers, or other objects for purposes of determining the user's gesture command and controlling the HMD 200, HMD controller 210, navigation controller 26, and/or manipulator controller 54 accordingly. Gesture commands can be used for any type of input used by the system 10.

In order for the HMD 200 to be effectively used, the HMD 200 must be registered to one or more objects used in the operating room, such as the tissue being treated, the surgical tool 22, the manipulator 12, the trackers 44, 46, 48, the localizer 34, and/or the like. In one embodiment, the HMD coordinate system is a global coordinate system (e.g., a coordinate system of the fixed surroundings as shown in FIG. 3). In this case, a local coordinate system LOCAL is associated with the HMD 200 to move with the HMD 200 so that the HMD 200 is always in a known position and orientation in the HMD coordinate system. The HMD 200 utilizes the four tracking sensors 212 to map the surroundings and establish the HMD coordinate system. The HMD 200 then utilizes the camera 214 to find objects in the HMD coordinate system. In some embodiments, the HMD 200 uses the camera 214 to capture video images of markers attached to the objects and then determines the location of the markers in the local coordinate system LOCAL of the HMD 200 using motion tracking techniques and then converts (transforms) those coordinates to the HMD coordinate system.

In another embodiment, a separate HMD tracker 218 (see FIG. 3), similar to the trackers 44, 46, 48, could be mounted to the HMD 200 (e.g., fixed to the support structure 202). The HMD tracker 218 would have its own HMD tracker coordinate system HMDTRK that is in a known position/orientation relative to the local coordinate system LOCAL or could be calibrated to the local coordinate system LOCAL using conventional calibration techniques. In this embodiment, the local coordinate system LOCAL becomes the HMD coordinate system and the transforms T7 and T8 would instead originate therefrom. The localizer 34 could then be used to track movement of the HMD 200 via the HMD tracker 218 and transformations could then easily be calculated to transform coordinates in the local coordinate system LOCAL to the localizer coordinate system LCLZ, the femur coordinate system FBONE, the manipulator coordinate system MNPL, or other coordinate system.

Referring back to FIG. 3, a registration device 220 may be provided with a plurality of registration markers 224 (shown in FIG. 1) to facilitate registering the HMD 200 to the localizer coordinate system LCLZ. The HMD 200 locates the registration markers 224 on the registration device 220 in the HMD coordinate system via the camera 214 thereby allowing the HMD controller 210 to create a transform T7 from the registration coordinate system RCS to the HMD coordinate system. The HMD controller 210 then needs to determine where the localizer coordinate system LCLZ is with respect to the HMD coordinate system so that the HMD controller 210 can generate images having a relationship to objects in the localizer coordinate system LCLZ or other coordinate system.

During use, for example, the localizer 34 and/or the navigation controller 26 sends data on an object (e.g., the cut volume model) to the HMD 200 so that the HMD 200 knows where the object is in the HMD coordinate system and can display an appropriate image in the HMD coordinate system. In embodiments in which the femur cut volume is to be visualized by the HMD 200, the localizer 34 and/or navigation controller 26 needs three transforms to get the femur cut volume data to the localizer coordinate system LCLZ, T9 to transform the femur cut volume coordinate system MODEL1 to the femur coordinate system FBONE, T5 to transform the femur coordinate system FBONE to the bone tracker coordinate system BTRK1, and T6 to transform the bone tracker coordinate system BTRK1 to the localizer coordinate system LCLZ. Once registration is complete, then the HMD 200 can be used to effectively visualize computer-generated images in desired locations with respect to any objects in the operating room.

II. Patient Specific Preoperative Simulation Techniques

Figure 4:
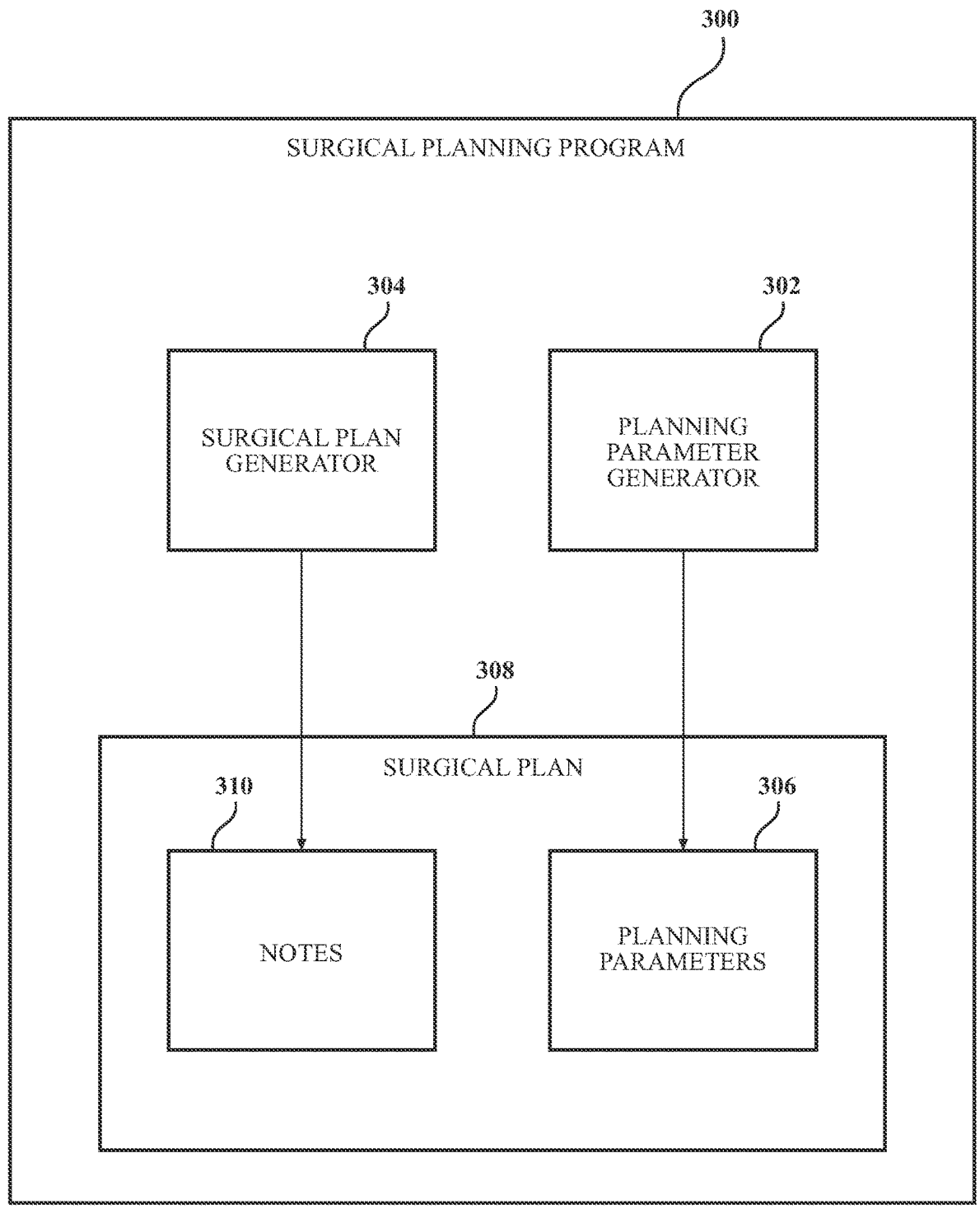
FIG. 4 is a block diagram of a surgical planning program.

FIG. 4 is a block diagram of a surgical planning program 300 that is stored within a non-transitory computer-readable medium, such as a memory accessible by the surgical system 10. The surgical planning program 300 may be used during a preoperative simulation of a surgical procedure to generate one or more planning parameters and/or a surgical plan to facilitate executing the procedure. In one embodiment, the surgical planning program 300 may be stored as a plurality of software instructions within a non-transitory storage medium of the navigation system 20. In such an embodiment, the instructions of the surgical planning program 300 may be executed by one or more processors, such as one or more processors of the navigation controller 26. Alternatively, the surgical planning program 300 may be stored in any suitable component or device of surgical system 10 and may be executed by any suitable processor of the surgical system 10. For example, the surgical planning program 300 may be stored within a simulation computer (not shown) that is used to perform or facilitate the simulation of the surgical procedure.

The surgical planning program 300 may include a planning parameter generator 302 and a surgical plan generator 304. The planning parameter generator 302 and the surgical plan generator 304 may be implemented as one or more software modules including instructions that are executable by one or more processors to perform the functions described herein.

The planning parameter generator 302 generates one or more planning parameters 306 during the simulation. In one embodiment, the planning parameters 306 may include one or more of a stereotactic or virtual boundary for the tool 22, a list of tools 22 used, a sequence of selection of tools 22 used, an amount of time that each tool was used 22, a feed rate of tool 22, a cutting speed of tool 22, an oscillation or rotation speed of tool 22, a path of tool 22 as tool 22 is moved (i.e., adjusted in pose) in relation to the anatomy (either virtual anatomy or physical anatomy), a pose of tool 22, a pose of tool 22 as tool 22 advances along the path, a force to be applied to tool 22, a damping to be applied to tool 22, a power to be applied to tool 22, an amount of material to be deposited by tool 22, a function to be executed by tool 22, and/or any other suitable parameters. In some embodiments, one or more planning parameters 306 physically modify the operation of the physical tool during the intraoperative surgery. For example, planning parameters 306 such as stereotactic boundaries and tool paths may be used by the manipulator 12 to constrain the movement of the tool 22 to follow the tool path or to prevent the tool 22 from crossing the stereotactic boundary.

As described herein, the surgical planning program 300 may generate the planning parameters 306 in a variety of ways. In one example, the surgical planning program 300 may receive inputs associated with one or more planning parameters 306 from the surgeon. For example, during the simulation of the surgical procedure, the surgeon may desire to create a stereotactic boundary for constraining movement of the tool 22. For example, the stereotactic boundary may ensure that the surgeon does not inadvertently operate the tool 22 in an undesired area of the patient's anatomy. The surgeon may use one or more of the input devices I to virtually draw or otherwise provide one or more reference points to define the boundary on the patient image data or on the model of the patient anatomy. The surgical planning program 300 may receive the inputs and may generate a planning parameter 306 representing the stereotactic boundary defined by the surgeon. In a similar manner, the surgical planning program 300 may receive other inputs from the surgeon representing planning parameters 306 to be used in the later intraoperative procedure. The surgical planning program 300 may capture these parameters 306 entered by the surgeon and may store the parameters 306 in the memory of the program 300.

In another embodiment, the surgical planning program 300 may automatically generate planning parameters 306 based on capturing movement of the tool 22 during the simulation. Such planning parameters 306 may be based on inputs from the navigation system 20 or from other devices or systems of the surgical system. The automatic generation of the planning parameters 306 may be accomplished autonomously by the surgical planning program 300 without input from the surgeon. For example, the surgical planning program 300 may receive inputs from the navigation system 20 corresponding to the tracked position of the tool 22 as the tool 22 is moved in relation to a model of an anatomy during the simulation. The surgical planning program 300 may generate a tool path from at least a portion of the tracked positions of the tool 22 and may store the tool path as a planning parameter 306 in memory. In some instances, input from the surgeon may be utilized to confirm or modify automatically generated planning parameters 306.

It should be recognized that the tool path generated from the tracked positions of the tool 22 may be more than a mere compilation of the raw position data received from the navigation system 20. For example, during the simulation, the surgeon may move the tool 22 at irregular intervals as the surgeon contemplates each stage of the workflow. Thus, the tool 22 may be positioned at different portions of the model of the anatomy for varying amounts of time. In one embodiment, the localizer 34 may be configured to periodically capture or sample the position of the tool 22 via the tool tracker 48 at regular time intervals. As a result, the raw position data received from the navigation system 20 may include a redundant number of position samples at various locations of the model of the anatomy. The surgical planning program 300 may remove or condense this redundant data and may otherwise generate a best-fit line, path, or surface that corresponds to the overall movement of the tool 22 in relation to the model of the anatomy. In a similar manner, the navigation system 20 may provide other inputs to the surgical planning program 300, and the surgical planning program 300 may then automatically generate respective planning parameters 306 based on the inputs received.

In one embodiment, the generation of the planning parameters 306 may use machine learning or artificial intelligence techniques to predictively generate one or more planning parameters 306. More specifically, the surgical planning program 300 may predictively generate one or more planning parameters 306 based on the inputs received from the surgical system 10. For example, the surgeon may move the tool 22 along a tool path that avoids nearby anatomical features during the simulation. The surgical planning program 300 may reference preoperatively generated patient image data to determine the anatomical features avoided by the surgeon and may automatically generate a stereotactic boundary at an edge of each anatomical feature avoided by the surgeon. The surgical planning program 300 may then store the generated stereotactic boundary as a planning parameter 306 in memory.

As another example, the surgeon may move the tool 22 in relation to the model of the anatomy according to several trial tool paths while deciding which path to use in performing the simulated procedure. The surgical planning program 300 may receive the various tracked movements of the tool 22 from the navigation system 20 and may determine that the surgeon has attempted different paths for the tool 22. The surgical planning program 300 may use machine learning or artificial intelligence techniques to model the most efficient tool path to take and may automatically generate a planning parameter 306 corresponding to the most efficient tool path.

In another example, the surgical planning program 300 may receive inputs from the manipulator controller 54 identifying the rotational speed of the tool 22 during various portions of the simulation. For example, the rotational speed of the tool 22 may be detected to be 50 revolutions per minute (RPM) at a first portion of the simulation, 20 RPM at a second portion of the simulation, and 50 RPM at a third portion of the simulation. The surgical planning program 300 may determine that a ceiling for the rotational speed of the tool 22 should be set at 50 RPM and a floor for the rotational speed of the tool 22 should be set at 20 RPM. Alternatively, the surgical planning program 300 may determine that an acceptable window for the rotational speed of the tool 22 is between 20 and 50 RPM. The surgical planning program 300 may then generate a planning parameter 306 for the rotational speed of the tool 22 even if the surgeon does not specify any requirement for the speed. Thus, the surgical planning program 300 may automatically generate planning parameters 306 relating to parameters of the surgical workflow that are not specifically input or identified by the surgeon. The above described example is merely illustrative, and other tools and/or other tool parameters (e.g., power, force, damping, etc.) may be determined and/or generated.

It should be recognized that the above-described embodiments of generating planning parameters 306 may be used in conjunction with each other, rather than solely as alternatives to each other. Thus, the surgical planning program 300 may receive some planning parameters 306 as inputs from the surgeon, may automatically generate other planning parameters 306 based on inputs from the surgical system 10, and may predictively generate still other planning parameters 306 based on inputs from the surgical system 10. In addition, the surgical planning program 300 may receive a portion of a planning parameter 306 as an input from the surgeon and may automatically generate the remaining portion of the planning parameter 300 based on inputs from the surgical system 10.

As described herein, the surgical plan generator 304 generates a surgical plan 308 for use in the intraoperative procedure. The surgical plan 308 may include a name of the surgical procedure, a list of surgical workflow steps involved in the procedure, planning parameters 306, notes 310, and/or any other suitable data.

In one embodiment, one or more notes 310 associated with one or more planning parameters 306 may be generated by the surgical planning program 300 and may be stored therein. The notes 310 may include, for example, reminders, warnings, memos, tips, recommendations, and the like. The foregoing examples are not meant to be limiting, but rather, the notes 310 may include any suitable text or graphic that may be displayed to the surgeon during the execution of the intraoperative procedure. In other embodiments, the notes 310 may include haptic, audio, or video notifications that may be presented to the surgeon during the intraoperative procedure.

As one example, a note 310 reminding the surgeon to exercise additional care in performing a particularly difficult portion of the surgical workflow may be generated. The note 310 may be associated with a particular portion of the tool path or stereotactic boundary relating to the difficult portion of the workflow, for example, such that the note 310 may be displayed to the surgeon when the surgeon reaches that point in the tool path or is in the process of removing patient tissue at or near the stereotactic boundary. In one embodiment, the surgeon may enter the notes as the surgeon performs the simulation, or before or after performing the simulation. The surgeon may operate an input device I, such as a keyboard and/or mouse, to enter the notes. Alternatively, the surgeon may speak the notes out loud and the system may use voice-recognition software to convert the spoken words of the surgeon into notes 310.

In addition, the surgeon may modify the planning parameters 306, the notes 310, and/or other portions of the surgical plan 308 after the portions of the surgical plan 308 have been generated. For example, the surgeon may initiate the performance of the surgical workflow during the simulation, and planning parameters 306 such as the tool path and pose of the tool 22 may be automatically generated by the surgical planning program 300. However, in the event the surgeon makes a mistake in operating the tool 22 or decides to modify the tool path or pose, the surgeon may "rewind" or "undo" the respective planning parameters 306. In such an example, the surgeon may use one or more input devices I to enter inputs into the surgical planning program 300 to revise the tool path and/or pose of the tool 22 to conform to a later-executed workflow that uses a different tool path and/or pose. The revised planning parameters 306, notes 310, and/or surgical plan 308 may be stored in the memory as part of the surgical planning program 300. The foregoing is merely one non-limiting example, and the surgical planning program 300 may enable the surgeon to revise any other planning parameter 306 as desired. The operation of the surgical planning program 300 is described in more detail in FIGS. 5 and 6.

Figure 5A:
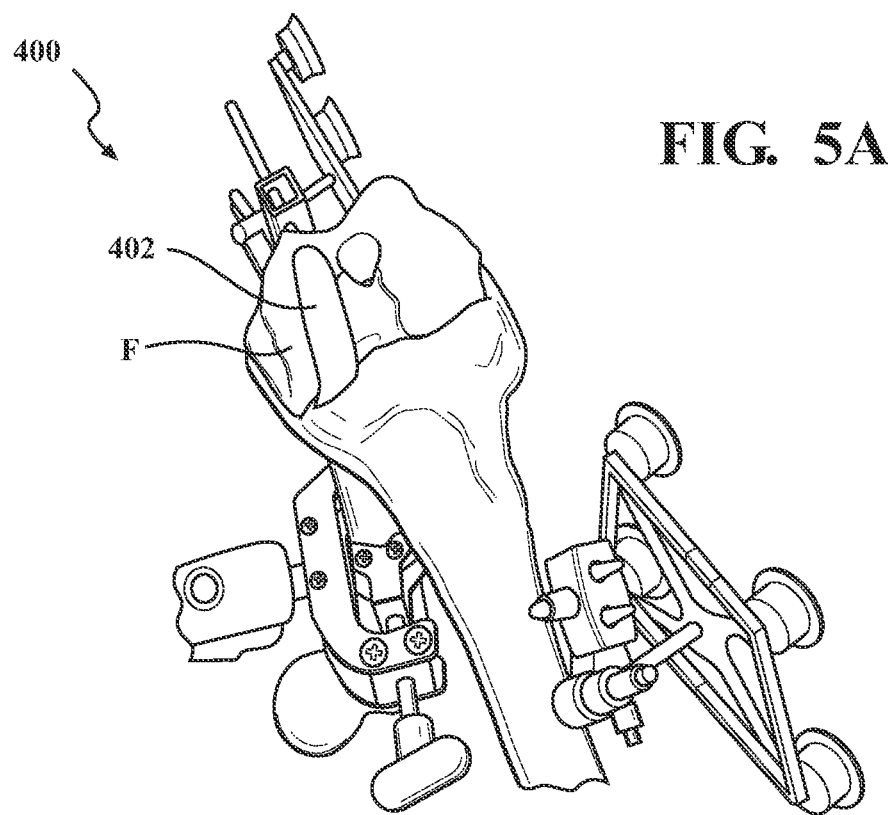
FIGS. 5A and 5B are perspective views of a preoperative simulation of a surgical procedure using a physical tool and a physical model of a patient's anatomy.
Figure 5B:
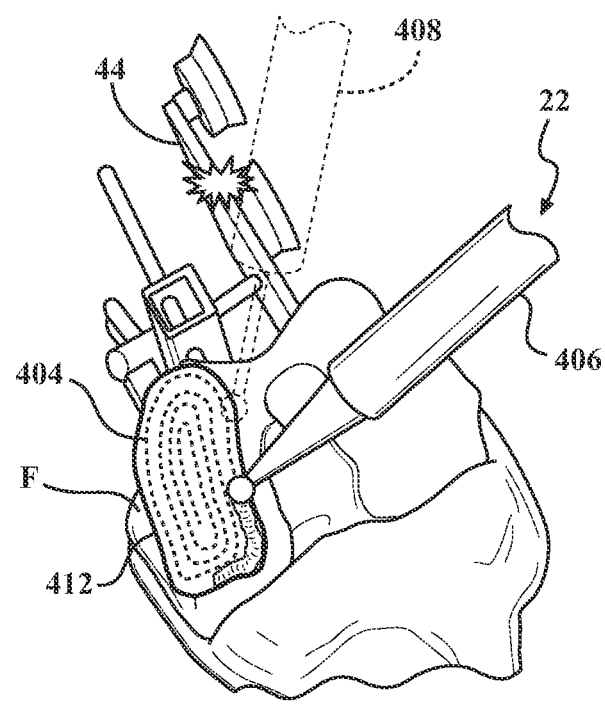

FIGS. 5A and 5B are perspective views of a physical model 400 of a patient's anatomy, which a surgeon is using to simulate a surgical procedure according to one example. In one embodiment, the simulation may be performed using the navigation system 20 or another suitable system or device of surgical system 10 that executes the surgical planning program 300 (shown in FIG. 4). Alternatively, the simulation may be performed on a separate simulation computer (not shown) that stores and executes the surgical planning program 300.

In the example shown in FIGS. 5A and 5B, the surgical procedure is a partial knee replacement surgical procedure. However, it should be recognized that any suitable surgical procedure may be simulated according to the present embodiments.

In the embodiment shown in FIGS. 5A and 5B, the surgeon is using a physical tool 22 to simulate the surgical procedure. Referring to FIG. 5A, one of the steps of the surgical workflow associated with the simulated surgical procedure is the removal of a target volume 402 of the patient's femur F. As illustrated in FIGS. 5A and 5B, for simulation purposes, a cast mold or other physical model of the patient's femur F is used.

As an initial step in the simulation, the model of the femur F and the tool 22 are registered in the localizer coordinate system LCLZ. More specifically, trackers 44, 46, 48 are firmly attached to the femur F, tibia T, and the tool 22, respectively (or to the manipulator 12 that holds the tool 22 in one embodiment). The localizer 34 registers the trackers 44, 46, 48 as described above with reference to FIGS. 1-3.

Referring to FIG. 5B, the surgeon may then operate the physical tool 22, moving the tool 22 in relation to the femur F. The movement of the tool 22 in relation to the femur defines a tool path 404. In addition, the surgeon may orient the tool 22 in one or more poses such that the tool 22 is oriented in a first pose 406 along a first portion of the tool path 404 and is oriented in a second pose 408 along a second portion of the tool path 404.

As the surgeon moves the tool 22, the navigation system 20 automatically tracks the movement to create the tool path 404. The navigation system 20 also automatically tracks the poses of the tool 22 as it moves along the tool path 404. The navigation system 20 provides the tracked movement and poses of the tool 22 as inputs to the surgical planning program 300 which then generates the tool path 404 and sequence of poses of the tool 22 during the simulation. The surgical planning program 300 stores planning parameters 306 associated with the tool path 404 and the sequence of poses in memory of the surgical planning program 300. In a similar manner, the navigation system 20 may provide other inputs to the surgical planning program 300, such as the sequence of tools 22 selected and used during the simulation. The surgical planning program 300 may then automatically generate respective planning parameters 306 based on the inputs received.

In another example, the surgical planning program 300 may automatically generate a virtual or stereotactic boundary 412 at the outer edge of the tool path 404 or at another suitable location. Alternatively, the surgeon may define the virtual boundary 412 by entering one or more inputs representative of the boundary 412 into the surgical planning program 300. The surgical planning program 300 may then store the boundary 412 in the memory of the program 300.

As described above, the surgeon may also dictate or otherwise provide one or more notes 310 during the simulation. For example, if the surgeon encounters unexpected difficulty in performing a particular step of the surgical workflow, the surgeon may enter a note 310 into the surgical planning program 300 identifying the difficulty and any tips or reminders of how to successfully complete that step of the workflow. The notes 310 may then be associated with the particular step of the workflow or with a particular portion of the tool path 404, for example.

After the surgeon is finished with the simulation of the surgical procedure, the surgeon may enter an input into the surgical planning program 300 indicating that the simulation is completed. In response to receiving the input, the surgical planning program 300 may stop generating planning parameters 306 and may generate the surgical plan 308 based on the previously generated notes 310 and parameters 306. The surgical planning program 300 may then store the completed surgical plan 308 in memory for later access during the intraoperative procedure.

While the embodiment described above uses the localizer to track the movement of the tool 22 and the anatomy to determine the tool path and/or other parameters 306, it should be recognized that other suitable methods for determining planning parameters 306 may be used. For example, in one embodiment, a scanner, optical sensor, or similar device (not shown) may be used to determine the locations of material removed from the physical model 400 of the patient's anatomy. More specifically, a scanner, optical sensor, or other suitable device may be used to determine an initial contour, shape, volume, and/or other similar characteristics of the physical model 400 of the anatomy before the simulation is performed. The characteristics may then be stored in memory for later comparison. After the surgeon has completed the simulation, the scanner, optical sensor, or other device may be used to determine the final contour, shape, volume, and/or other characteristic of the physical model 400. The surgical planning program may then compare the final characteristic with the initial characteristic to determine an amount of material removed from the model 400, one or more stereotactic boundaries for the tool 22, and/or any other suitable parameter 306.

Figure 6:
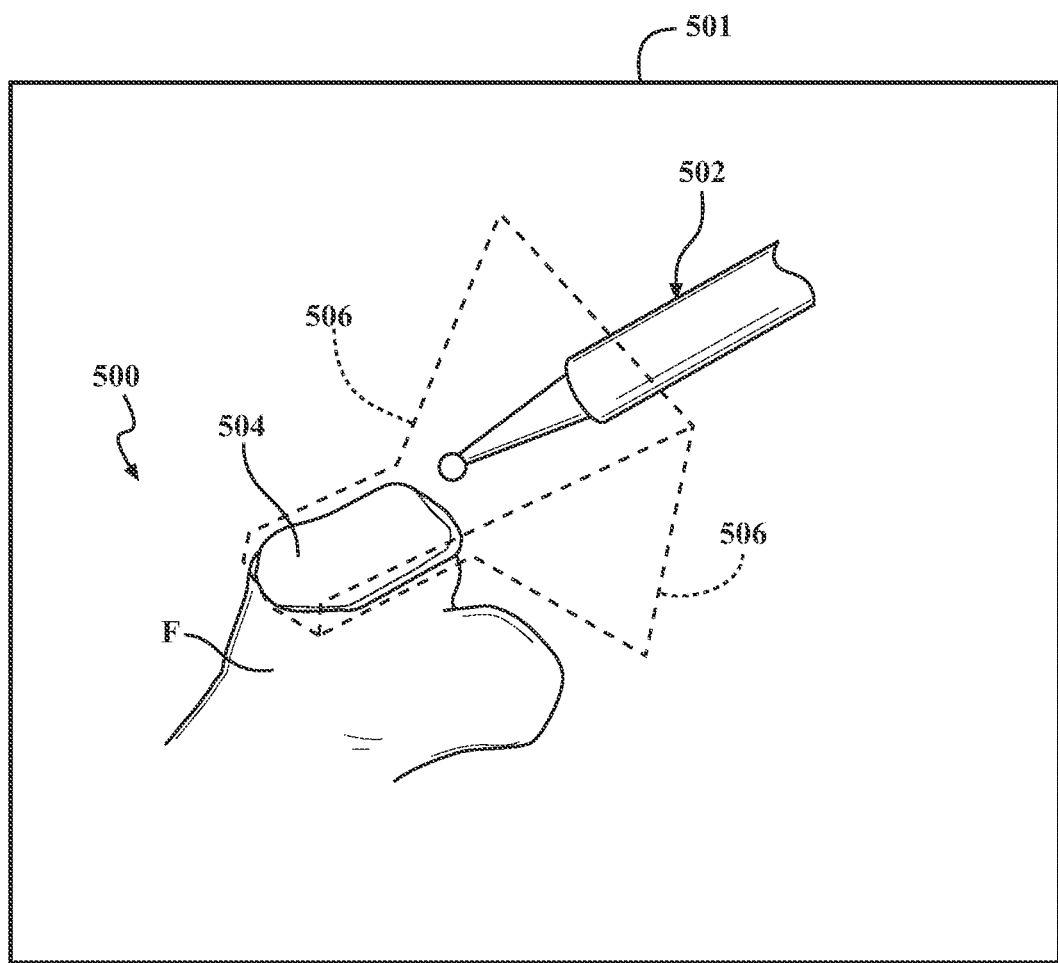
FIG. 6 is a perspective view of a preoperative simulation of a surgical procedure using a virtual tool and a virtual model of the patient's anatomy.

FIG. 6 is a perspective view of a virtual model 500 of a patient's anatomy which a surgeon is using to simulate a surgical procedure. In one embodiment, the simulation may be performed using the navigation system 20 or another suitable system or device of surgical system 10 that executes the surgical planning program 300 (shown in FIG. 4). Alternatively, the simulation may be performed on a separate simulation computer (not shown) that stores and executes the surgical planning program 300.

In the embodiment shown in FIG. 6, the virtual model 500 is displayed within a display 501. In one embodiment, the display 501 is one or more of the displays 28, 29. Alternatively, the display 501 may be part of HMD 200 or another suitable display. As illustrated in FIG. 6, the virtual model 500 may be a three-dimensional model or other visual representation of patient image data that was preoperatively acquired via MRI, CT, or another suitable imaging modality. Thus, in this embodiment, the virtual model is a representation of the anatomy of the patient that will later undergo the surgical operation that is being simulated in FIG. 6. While FIG. 6 illustrates a three-dimensional model of the patient's anatomy, it should be recognized that the patient image data may be alternatively displayed as a two-dimensional image of the patient's anatomy. In the example shown in FIG. 6, the surgical procedure is a partial knee replacement surgical procedure. However, it should be recognized that any suitable surgical procedure may be simulated according to the present embodiments.

In the embodiment shown in FIG. 6, the surgeon is using a virtual representation 502 of a physical tool 22 (hereinafter referred to as a virtual tool 502) to simulate the surgical procedure. Thus, in one embodiment, the virtual tool 502 is a three-dimensional model of the tool 22 that will later be used in the execution of the intraoperative surgical procedure that is currently being simulated. Alternatively, the virtual tool 502 may be displayed as a two-dimensional image of the physical tool 22 that will later be used to perform the intraoperative procedure. The virtual tool 502 may be displayed in relation to the virtual model 500 of the anatomy within display 501.

In one embodiment, one of the steps of the surgical workflow associated with the simulated surgical procedure may be the removal of a target volume 504 of the patient's femur F. The surgeon may operate the virtual tool 502 by entering inputs into the surgical planning program 300 using one or more input devices I of the navigation system 20 representing a desired change in position or pose of the tool 502. In response, the surgical planning program 300 moves the virtual tool 502 in relation to the image of the femur F. The movement of the tool 502 in relation to the femur defines a virtual tool path 506. In addition, the surgeon may orient the virtual tool 502 in one or more poses in a similar manner as described above.

The surgeon may also operate one or more input devices I to adjust the resolution of the patient image data. For example, the surgeon may "zoom" in or out of the patient image data and may adjust the viewing perspective of the image data to provide a desired viewpoint and resolution to the surgeon.

As the surgeon moves the virtual tool 502, the surgical planning program 300 tracks the change in pose of the tool as the tool moves along the tool path. The surgical planning program 300 stores planning parameters 306 associated with the tool path 506 and the sequence of poses in memory of the surgical planning program 300. In a similar manner, the surgical planning program 300 may automatically generate other planning parameters 306 in a similar manner as described above.

As described above, the surgeon may also dictate or otherwise provide one or more notes 310 during the simulation. The notes 310 may then be associated with the particular step of the workflow or with a particular portion of the tool path 506, for example.

Figure 7:
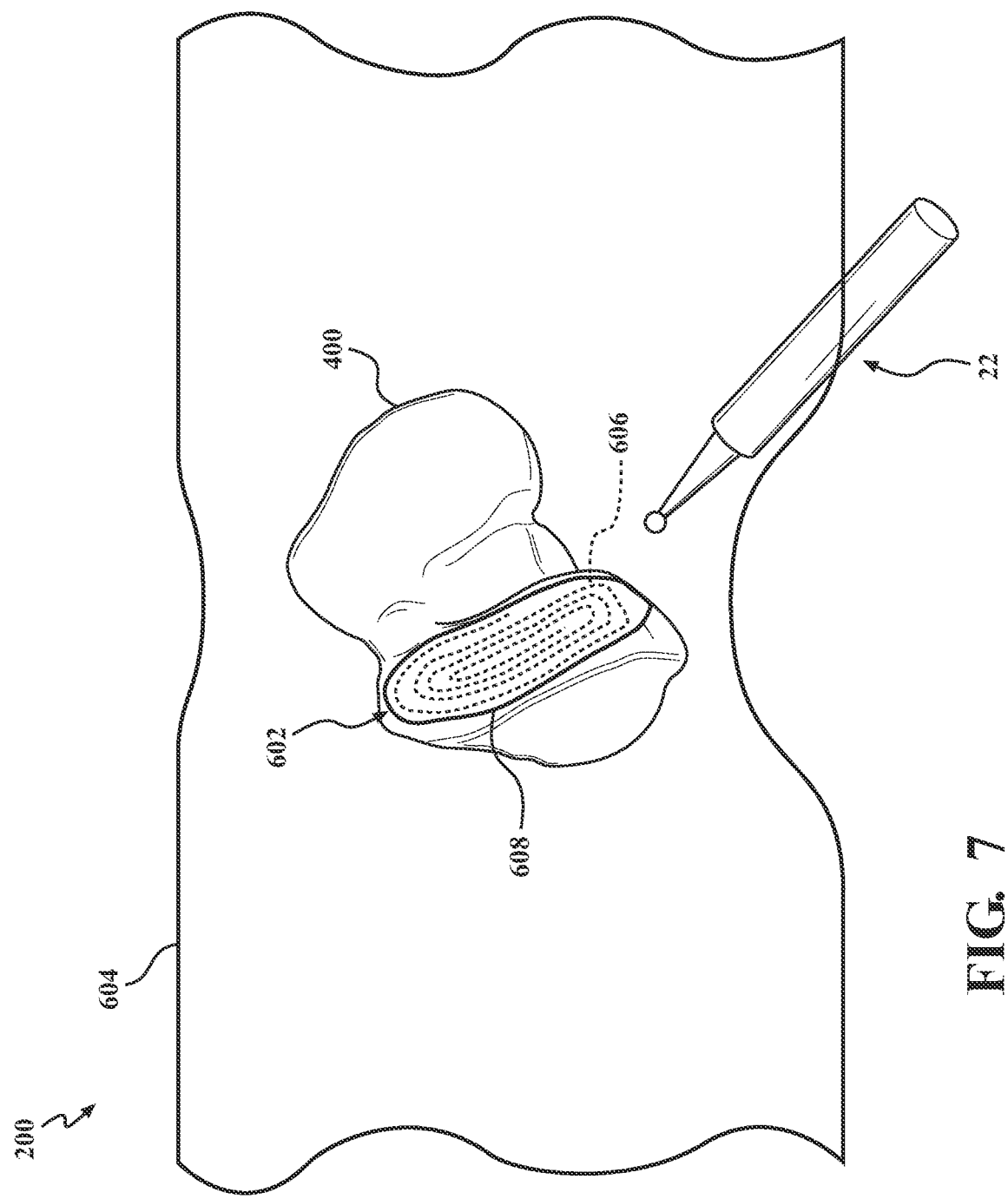
FIG. 7 is a perspective view of a preoperative simulation of a surgical procedure using a physical tool with a virtual model of the patient's anatomy.

FIG. 7 is a perspective view of a virtual model 400 of a patient's anatomy, which a surgeon is using to simulate a surgical procedure using a physical tool 22 according to one example. In one embodiment, the physical tool 22 is a surgical tool that is the same as, or similar to, the actual surgical tool that will be used in the later intraoperative procedure. In an alternative embodiment, the physical tool 22 may be a handheld wand or other device that is tracked by a camera (e.g., the camera unit 36) or other tracking sensor. In the alternative embodiment, the tool may include an integrated infrared or other marker that may cooperate with the tracking sensor to track the pose of the tool over time. When viewed using a head mounted display (HMD) 200 or the like, a virtual graphical representation of the surgical tool may be displayed to the user by the HMD 200. In one embodiment, the simulation may be performed using the navigation system 20 or another suitable system or device of surgical system 10 that executes the surgical planning program 300 (shown in FIG. 4). Alternatively, the simulation may be performed on a separate simulation computer (not shown) that stores and executes the surgical planning program 300.

In the embodiment shown in FIG. 7, the surgeon is using a physical tool 22 to simulate the surgical procedure. One of the steps of the surgical workflow associated with the simulated surgical procedure is the removal of a target volume 602 of the patient's femur F. As illustrated in FIG. 7, for simulation purposes, a virtual model 400 of a portion of the patient's femur F is used.

In the embodiment shown in FIG. 7, the virtual model 400 is displayed by a display 604. In one embodiment, the display 604 is part of HMD 200 or another suitable display. For example, the virtual model 400 may be displayed on one or more display screens (e.g., eyeglass lenses) of the HMD 200 as the HMD 200 is worn by the surgeon. As illustrated in FIG. 7, the virtual model 400 may be a three-dimensional model or other visual representation of patient image data that was preoperatively acquired via MRI, CT, or another suitable imaging modality. Thus, in this embodiment, the virtual model 400 is a representation of the anatomy of the patient that will later undergo the surgical operation that is being simulated in FIG. 7. In the example shown in FIG. 7, the surgical procedure is a partial knee replacement surgical procedure. However, it should be recognized that any suitable surgical procedure may be simulated according to the present embodiments.

As an initial step in the simulation, the virtual model 400 of the femur F and the tool 22 are registered in the localizer coordinate system LCLZ. More specifically, trackers 48, 218 are coupled to the tool 22 and the HMD 200 respectively (or to the manipulator 12 that holds the tool 22 in one embodiment). The localizer 34 registers the trackers 48, 218 as described above with reference to FIGS. 1-3. Once the HMD 200 is registered within the localizer coordinate system LCLZ, the virtual model 400 of the patient's anatomy is likewise registered to the localizer coordinate system LCLZ. In one embodiment, the HMD 200 and virtual model are registered to the localizer coordinate system LCLZ as described in U.S. patent application Ser. No. 15/860,057, entitled "Systems and Methods for Surgical Navigation", the disclosure of which is incorporated by reference in its entirety.

The surgeon may then operate the physical tool 22, moving the tool 22 in relation to the virtual model 400. As the surgeon moves the tool 22, the navigation system 20 automatically tracks the movement to create a tool path 606. The navigation system 20 also automatically tracks the poses of the tool 22 as it moves along the tool path 606 in a similar manner as described above with reference to FIGS. 5A and 5B. The navigation system 20 provides the tracked movement and poses of the tool 22 as inputs to the surgical planning program 300 which then generates the tool path 606 and sequence of poses of the tool 22 during the simulation. The surgical planning program 300 stores planning parameters 306 associated with the tool path 606 and the sequence of poses in memory of the surgical planning program 300. In a similar manner, the navigation system 20 may provide other inputs to the surgical planning program 300, such as the sequence of tools 22 selected and used during the simulation. The surgical planning program 300 may then automatically generate respective planning parameters 306 based on the inputs received. Accordingly, the surgical planning program 300 may generate one or more planning parameters 306 based on the use of the physical tool 22 in relation to the image representing the portion of the patient's anatomy as displayed by the display 604.

In another example, the surgical planning program 300 may automatically generate a virtual or stereotactic boundary 608 at the outer edge of the tool path 606 or at another suitable location. Alternatively, the surgeon may define the virtual boundary 608 by entering one or more inputs representative of the boundary 608 into the surgical planning program 300. The surgical planning program 300 may then store the boundary 608 in the memory of the program 300.

As described above, the surgeon may also dictate or otherwise provide one or more notes 310 during the simulation. For example, if the surgeon encounters unexpected difficulty in performing a particular step of the surgical workflow, the surgeon may enter a note 310 into the surgical planning program 300 identifying the difficulty and any tips or reminders of how to successfully complete that step of the workflow. The notes 310 may then be associated with the particular step of the workflow or with a particular portion of the tool path 606, for example.

After the surgeon is finished with the simulation of the surgical procedure, the surgeon may enter an input into the surgical planning program 300 indicating that the simulation is completed. In response to receiving the input, the surgical planning program 300 may stop generating planning parameters 306 and may generate the surgical plan 308 based on the previously generated notes 310 and parameters 306. The surgical planning program 300 may then store the completed surgical plan 308 in memory for later access during the intraoperative procedure.

Figure 8:
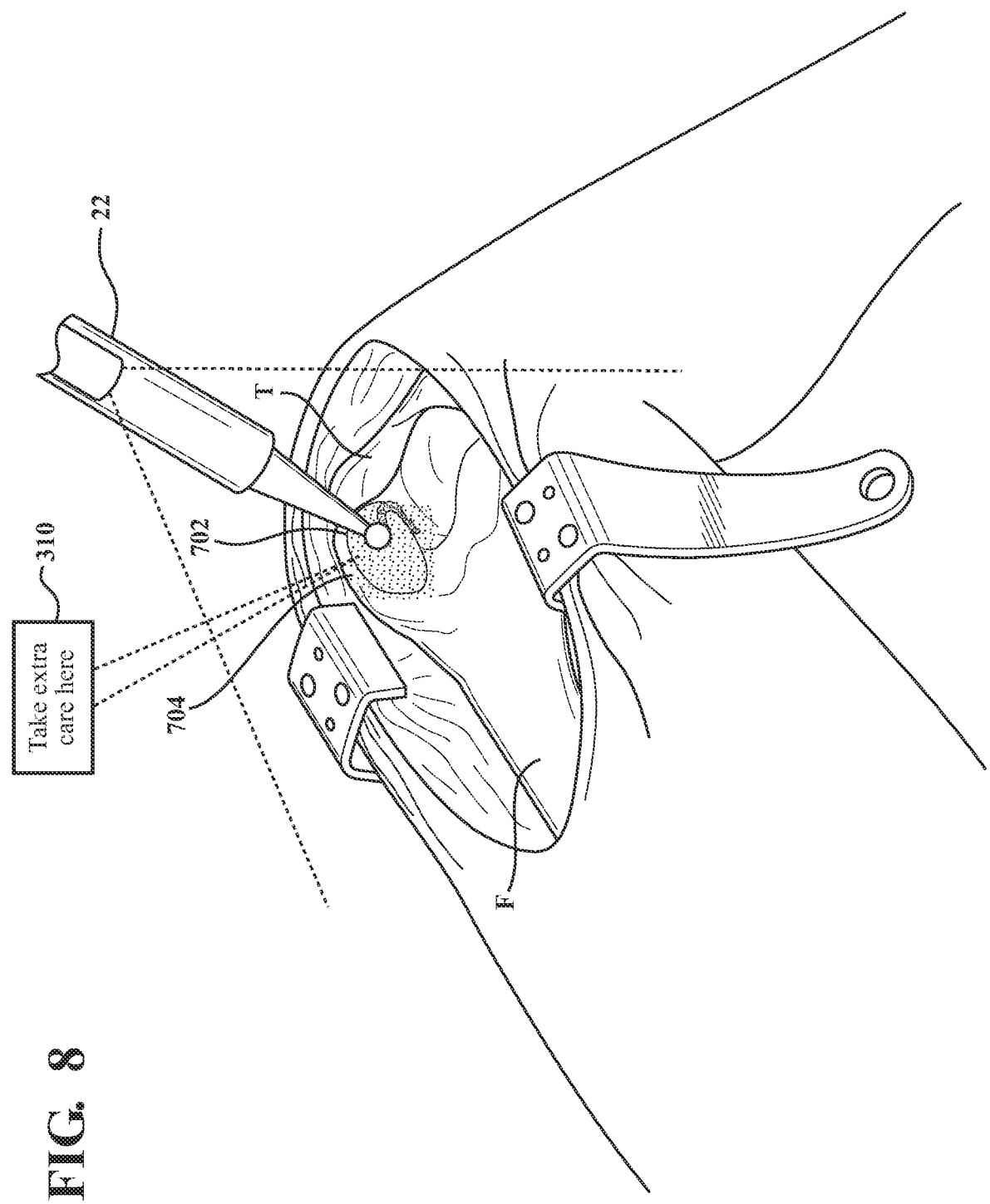
FIG. 8 is a perspective view of a patient's anatomy during execution of an intraoperative surgical procedure.
Figure 9:
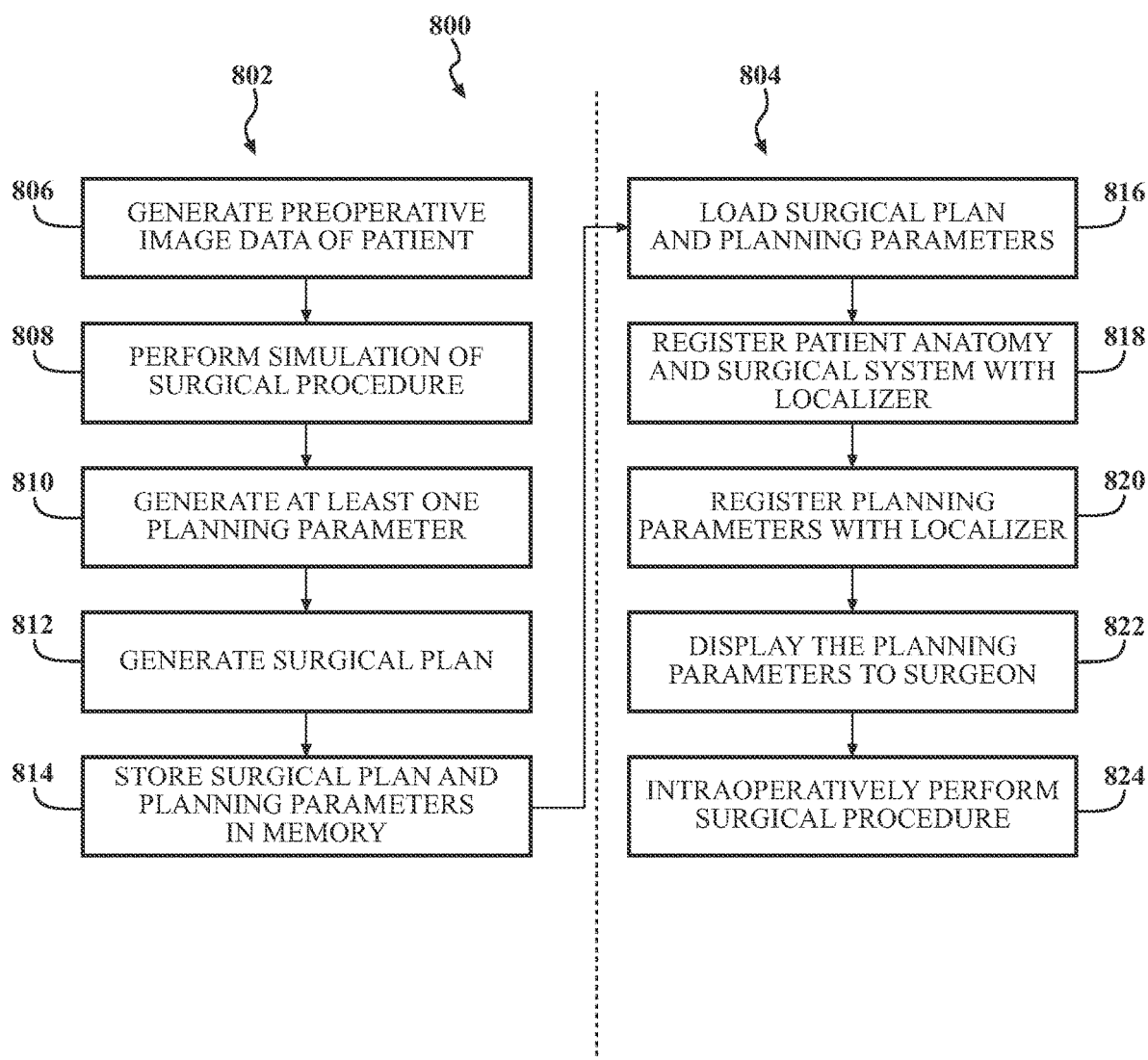
FIG. 9 is a flowchart of a method of executing a surgical procedure.

FIG. 8 is a perspective view of a portion of a patient's anatomy while the patient is undergoing an intraoperative surgical procedure. In a specific embodiment, the patient is undergoing the surgical procedure that the surgeon simulated in accordance with the embodiments described in FIGS. 5A and 5B or in FIG. 6. Accordingly, the patient is undergoing a partial knee replacement surgical operation in the illustrated embodiment. However, it should be recognized that any suitable intraoperative surgical procedure may be performed that substantially matches the surgical procedure that was simulated preoperatively.

As described herein, the intraoperative surgical procedure is executed using system 10 (shown in FIG. 1). One way that the intraoperative surgical procedure may be executed is described in U.S. patent application Ser. No. 15/860,057, entitled "Systems and Methods for Surgical Navigation", the disclosure of which is incorporated herein by reference. While the following embodiments are described as being performed with the assistance of the manipulator 12 in a semi-autonomous mode of operation, it should be recognized that the embodiments may alternatively be performed without the use of the manipulator 12. For example, the surgeon may operate one or more surgical tools 22 manually while viewing one or more of the planning parameters 306 and/or notes 310 on a display, such as a display of HMD 200 and/or a display 28 or 29 of the navigation system 20. It should also be recognized that the manipulator 12 may perform the surgical procedure in an autonomous mode of operation in which the manipulator removes the target volume of the anatomy, rather than the surgeon. Notwithstanding the foregoing, the following embodiments will be described with reference to the semi-autonomous mode of operation unless otherwise specified.

As the surgeon prepares to execute the intraoperative surgical procedure, the navigation controller 26 and/or the manipulator controller 54 loads the surgical plan 308 along with the planning parameters 306 and any notes 310 that were generated during the simulation. As noted above, the planning parameters 306 may include a tool path and a pose of the tool 22 at each portion of the tool path.

Since the planning parameters 306 were generated using the surgical planning program 300 described above, the planning parameters 306 will need to be registered to the navigation system of coordinates (i.e., the localizer coordinate system LCLZ). To accomplish this, the patient's anatomy is first registered by affixing trackers 44, 46 to the femur F and tibia T. The anatomy is then registered by the localizer 34 in a manner described above with reference to FIGS. 1-3. In a similar manner, the tool 22 and/or the manipulator 12 to which the tool 22 is attached is registered to tracker 48 affixed to the tool 22 or manipulator 12.

If the preoperative simulation was performed using a virtual tool 502 in relation to a virtual model 500 of the patient's anatomy, the virtual model 500 of the patient's anatomy may be matched to the actual patient's anatomy using a method similar to that described in U.S. Pat. No. 8,675,939, entitled "Registration of Anatomical Data Sets", the disclosure of which is hereby incorporated by reference in its entirety. On the other hand, if the preoperative simulation was performed using a physical tool 22 in relation to a physical model 400 of the patient's anatomy, the registration data used by the localizer 34 during the simulation may be correlated to the registration data used by the localizer 34 described in the preceding paragraph according to methods known in the art. Once the virtual or physical model of the patient's anatomy used in the simulation is correlated to the intraoperative registration data of the localizer 34, the coordinates of the tool path and other planning parameters 306 may be transformed according to known methods. After this, the planning parameters 306 are represented in the localizer coordinate system LCLZ.

Once the planning parameters 306 are registered and represented in the localizer coordinate system LCLZ, the planning parameters 306, notes 310, and/or other portions of the surgical plan 308 may be displayed to the surgeon during the execution of the intraoperative surgical procedure. The planning parameters 306 and other portions of the surgical plan 308 may be displayed on any suitable display, such as the display 28 or 29, on HMD 200, and/or as a holographic image overlaid onto the patient's anatomy or on a wall or other portion of the system 10. The following embodiments are described with reference to the display of the planning parameters 306 on HMD 200 with the understanding that the embodiment may equally apply to other displays with appropriate modifications.

In an embodiment in which HMD 200 is used, the HMD 200 must also be registered to the localizer coordinate system LCLZ. The HMD 200 may be registered using HMD tracker 218 in a similar manner as described above with reference to FIGS. 1-3. In addition, the HMD 200 may be tracked and registered in a similar manner as described in U.S. patent application Ser. No. 15/602,261, entitled "Systems and Methods for Identifying and Tracking Physical Objects During A Robotic Surgical Procedure", the disclosure of which is hereby incorporated by reference in its entirety.

According to one example illustrated in FIG. 8, the HMD 200 can be used to visually depict the desired tool path for the tool 22 to follow during manual, semi-autonomous, or autonomous movement of the surgical tool 22. The navigation controller 26 and/or the manipulator controller 54 can store the tool path and its associated location data. This location data is transmitted to the HMD controller 210, which generates a tool path image 702 visually coinciding with the stored tool path such that the HMD 200 displays the tool path image 702 to seemingly be located in the actual bone at the actual locations that the working end of the tool 22 (e.g., the bur) will traverse along the tool path. The entire tool path can be displayed to the surgeon or only portions of the tool path might be displayed, such as only those portions that have not yet been traversed. In some cases, as the working end of the tool 22 successfully follows along segments of the tool path, images associated with those segments may disappear and no longer be displayed. In some cases, only a small section of the tool path is displayed ahead of the working end of the surgical tool 22 to act as a general guide, but not the entire tool path.

In a similar manner, data representative of the desired pose of the surgical tool 22 can be provided to the HMD controller 210 so that the HMD controller 210 can generate corresponding pose (i.e., position and/or orientation) images along one or more segments of the tool path to visually depict to the surgeon how the surgical tool 22 should be positioned and/or oriented in the future with respect to the actual anatomy.

According to another embodiment, the HMD 200 may also be used to visually depict planning parameters 306 representative of virtual or stereotactic boundaries 704 associated with the particular treatment of the patient. If the working end of the surgical tool 22 moves near and/or outside of this virtual boundary 704, haptic feedback may be generated via the manipulator 12 in the manner described in U.S. Pat. No. 8,010,180, entitled, "Haptic Guidance System and Method", the disclosure of which is hereby incorporated by reference. This haptic feedback indicates to the user that the working end of the surgical tool 22 is approaching the virtual boundary 704, has reached the boundary 704, or is beyond the boundary 704. In some cases, the boundary 704 is represented as a path, such as a trajectory along which the surgical tool 22 is expected to be oriented and/or along which the surgical tool 22 is expected to traverse. In this case, the haptic feedback may indicate to the user that the surgical tool 22 has been reoriented off the trajectory or has moved too far along the trajectory.

In a similar manner, any other suitable planning parameter 306 may be displayed to the surgeon during the intraoperative surgical procedure on HMD 200. The HMD 200 may also display any notes 310 that were generated during the preoperative simulation. In one embodiment, each note 310 is only displayed when the surgeon reaches the workflow step associated with the note 310. In a further embodiment, one or more notes 310 may be audibly presented to the surgeon by a speaker within the surgical system 10 instead of, or in addition to, the note 310 being visually displayed on HMD 200.

Accordingly, as described herein, the display of the planning parameters 306, notes 310, and/or other aspects of the surgical plan 308 may assist the surgeon in performing the intraoperative surgical procedure and may reduce a number and/or severity of errors that may otherwise occur during the surgical procedure.

FIG. 8 is a flowchart illustrating a method 800 of performing a surgical procedure on a patient. In one embodiment, one or more steps of the method 800 are embodied as a plurality of instructions that are stored in a non-transitory computer-readable medium and that are executable by a processor. For example, the method 800 may be at least partially executed by the surgical system 10 when a processor, such as navigation controller 26 and/or manipulator controller 54, execute the instructions associated with one or more steps. In a further embodiment, at least some of the steps of the method 800 may be automatically executed by the surgical planning program 300 (shown in FIG. 4).

In an embodiment, the method 800 is split into two main flows: a preoperative simulation flow 802 and an intraoperative flow 804. The preoperative flow 802 begins with generating 806 preoperative image data of a patient. For example, preoperative image data may be generated using an MRI system, a CT system, a PET system, an x-ray fluoroscopy system, and/or any other suitable system.

A preoperative simulation of the surgical procedure may then be performed 808. As part of the preoperative simulation flow 802, one or more components of the surgical system 10 may need to be registered using the localizer 34. For example, if the surgeon is using a physical tool 22 to simulate the surgical procedure on a physical model of the patient's anatomy, the physical tool 22 and the physical model of the patient's anatomy may be registered in a similar manner as described above. Alternatively, in an embodiment where the surgeon is operating a virtual representation of a physical tool on a virtual model of the patient's anatomy during the simulation, no registration of the virtual tool or virtual model of the anatomy is required.

As the surgeon performs the steps of the surgical workflow associated with the surgical procedure, at least one planning parameter is automatically generated 810. For example, the surgical planning program 300 may automatically generate a tool path based on the change in pose of the tool by the surgeon as the surgeon performs the steps of the surgical workflow. One or more notes may also be generated as described above.

After the simulation has completed or after the surgeon has completed simulating the steps of the surgical workflow, the surgical planning program may generate 812 a surgical plan based on the planning parameters 306 and/or any notes 310 generated, for example. The surgical plan 308 and its associated planning parameters 306, notes 310, and other components may then be stored 814 in memory for later retrieval to assist the surgeon in performing the intraoperative procedure.

During the intraoperative flow 804, the surgical plan 308 and its included planning parameters 306 and notes 310 are loaded 816 from the surgical planning program. The patient's anatomy and the surgical system 10 may be registered 818 with the localizer 34 in a similar manner as described above. This step includes firmly attaching trackers 44, 46 to the patient's anatomy. Alternatively, any suitable number of trackers may be attached to any suitable portion or portions of the patient's anatomy. This step also includes firmly attaching tracker 48 to tool 22 or manipulator 12, and optionally attaching HMD tracker 218 to HMD 200 in embodiments where the HMD 200 is used. The registration of the various trackers and the transforms applied to the localizer signals received from each tracker is described above with reference to FIGS. 1-3.

The planning parameters 306 and any other portions of the surgical plan that relate to coordinates are also registered 820 with the localizer. The registration of the planning parameters 306 includes applying a transform to the parameters to transform them from the surgical planning program coordinate system to the localizer coordinate system LCLZ in a similar manner as described above. Example parameters 306 that may be registered include a tool path, a pose of tool 22, and a stereotactic boundary for the tool 22.

The planning parameters 306 are displayed 822 to the surgeon during the intraoperative execution of the surgical procedure. This step may include displaying the parameters 306 on the HMD 200, displaying the parameters 306 on one or more of the displays 28, 29, and/or projecting a holographic image of one or more parameters 306 onto the patient's anatomy or onto a suitable portion of the surgical system 10.

The surgeon then intra-operatively performs 824 or executes the surgical procedure while one or more of the parameters 306 and notes 310 are displayed to the surgeon. As the surgeon performs or executes the procedure, the navigation system 20 tracks the real-time pose of the tool 22 and automatically updates at least one parameter 306 based on the real-time pose. For example, as the surgeon advances the tool 22 along the tool path, the HMD 200 receives the tracking data from the navigation system 20 and automatically displays the tool path as being traversed as the surgeon advances the tool 22 along the tool path. For example, the tool path that has already been followed may be displayed in a first color, such as green, and the tool path that the surgeon has not yet followed or completed may be displayed in a second color, such as red. In another example, as the surgeon advances the tool 22 along the tool path, the system may determine that the surgeon has completed a particular stage of the surgical plan and may display a note 310 or other data indicating the completion of the stage. The system may then display a note 310 or other data indicating the next stage of the surgical plan that must be completed as well as additional notes 310 or other data indicating tips, warnings, instructions, or supplemental data relating to the upcoming stage. As another example, the system may automatically determine, based on the tracked pose of the tool 22, that the surgeon has deviated from the tool path or from another planning parameter, or is at risk of doing so, and may display a warning, error, or other notification indicating such.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical system comprising:
a head-mounted device (HMD) comprising an HMD controller and a display that is configured to be located in front of eyes of a wearer of the HMD;
a navigation system comprising a localizer and a bone tracker coupled to a physical bone of a patient, wherein the localizer comprises a localizer coordinate system and is configured to monitor the bone tracker to track a pose of the physical bone in the localizer coordinate system, wherein the navigation system is configured to:
obtain surgical plan data related to the physical bone, wherein the surgical plan data comprises a virtual model of the physical bone, cut volume data defining material to be removed from the physical bone in preparation for receiving an implant, and a textual note previously created by a surgeon during surgical planning related to the physical bone, wherein the textual note is associated with a particular surgical step related to the physical bone;
register the HMD to the localizer coordinate system using the localizer such that the localizer is able to obtain a pose of the HMD; and
transmit the surgical plan data to the HMD controller; and
wherein the HMD controller is configured to:
provide, on the display, computer-generated imagery representative of the surgical plan data, including the virtual model of the physical bone and the cut volume data;
align and combine the computer-generated imagery with a real-world view of the physical bone; and
automatically present, on the display, the textual note at the time of the particular surgical step with which the textual note is associated.

2. The surgical system of claim 1, wherein the HMD controller aligns the computer-generated imagery with the real-world view of the physical bone in accordance with the tracked pose of the physical bone and the pose of the HMD.

3. The surgical system of claim 1, wherein the navigation system is configured to register the surgical plan data to the localizer coordinate system through combination of:
a first transform defining a relationship between the physical bone and the bone tracker; and
a second transform defining a relationship between the bone tracker and the localizer.

4. The surgical system of claim 1, wherein:
the HMD further comprises a video camera;
the navigation system further comprises a registration device including a plurality of registration markers that are detectable by the localizer and by the video camera of the HMD; and
the navigation system is configured to register the HMD to the localizer coordinate system through combination of a first transform defining a relationship between the HMD and the registration device and a second transform a relationship between the registration device and the localizer.

5. The surgical system of claim 1, wherein:
the navigation system comprises an HMD tracker coupled to the HMD; and
the navigation system is configured to register the HMD to the localizer coordinate system through detection of a pose of the HMD tracker.

6. The surgical system of claim 1, wherein the HMD further comprises a video camera, and wherein the real-world view is further defined as a real-world video captured by the video camera of the HMD.

7. The surgical system of claim 1, wherein:
the surgical plan data further comprises a size of the implant and/or a placement of the implant; and
the HMD controller is configured to further provide, on the display, computer-generated imagery representative of the surgical plan data, including the size of the implant and/or the placement of the implant.

8. The surgical system of claim 1, further comprising a surgical tool that is configured to remove the material from the physical bone in preparation for receiving the implant, and wherein:
the navigation system further includes a tool tracker coupled to the surgical tool;
the navigation system is configured to monitor the tool tracker to track poses of the surgical tool in the localizer coordinate system; and
the HMD controller is configured to provide, on the display, computer-generated imagery representative of the surgical tool relative to the computer-generated imagery including the virtual model of the physical bone and the cut volume data.

9. The surgical system of claim 8, wherein the cut volume data further comprises a virtual cutting boundary that defines the material to be removed from the physical bone, wherein the virtual cutting boundary is designed to prevent the surgical tool from removing material from an undesired area of the patient.

10. The surgical system of claim 9, wherein the surgical tool is hand-held.

11. The surgical system of claim 1, further comprising a manipulator comprising a base and a robotic arm extending from the base, wherein the robotic arm is configured to support and move a surgical tool that is configured to remove the material from the physical bone in preparation for receiving the implant, and wherein:
the navigation system further includes a tracker coupled to the manipulator;
the navigation system is configured to monitor the tracker to track a pose of the surgical tool in the localizer coordinate system; and
the HMD controller is configured to further provide, on the display, computer-generated imagery representative of the surgical tool relative to the computer-generated imagery including the virtual model of the physical bone and the cut volume data.

12. The surgical system of claim 11, wherein the cut volume data further comprises a virtual cutting boundary that defines the material to be removed from the physical bone, wherein the virtual cutting boundary is designed to prevent the surgical tool from removing material from an undesired area of the patient.

13. The surgical system of claim 11, wherein:
the surgical plan data further comprises a tool path along which the manipulator moves, or will move, the surgical tool to remove the material from the physical bone in preparation for receiving the implant; and the HMD controller is configured to further provide, on the display, computer-generated imagery representative of the tool path relative to the computer-generated imagery including the virtual model of the physical bone and the cut volume data.

14. The surgical system of claim 1, wherein the HMD further comprises a sensor configured to recognize gesture commands from the wearer of the HMD, and wherein the HMD controller is configured to detect the gesture commands to enable modification to the surgical plan data.

15. The surgical system of claim 1, wherein the display of the HMD is further defined as an organic light-emitting diode display.

16. A method of operating a surgical system, the surgical system comprising a head-mounted device (HMD) including an HMD controller and a display that is configured to be located in front of eyes of a wearer of the HMD, a navigation system including a localizer and a bone tracker coupled to a physical bone of a patient, wherein the localizer comprises a localizer coordinate system and is configured to monitor the bone tracker to track a pose of the physical bone in the localizer coordinate system, the method comprising:

with the navigation system:
obtaining surgical plan data related to the physical bone, wherein the surgical plan data comprises a virtual model of the physical bone, cut volume data defining material to be removed from the physical bone in preparation for receiving an implant, and a textual note previously created by a surgeon during surgical planning related to the physical bone, wherein the textual note is associated with a particular surgical step related to the physical bone;
registering the HMD to the localizer coordinate system using the localizer such that the localizer is able to obtain a pose of the HMD; and
transmitting the surgical plan data to the HMD controller; and with the HMD controller:
providing, on the display, computer-generated imagery representative of the surgical plan data, including the virtual model of the physical bone and the cut volume data;
aligning and combining the computer-generated imagery with a real-world view of the physical bone; and
automatically presenting, on the display, the textual note at the time of the particular surgical step with which the textual note is associated.

17. The method of claim 16, comprising the HMD controller aligning the computer-generated imagery with the real-world view of the physical bone in accordance with the tracked pose of the physical bone and the pose of the HMD.

18. The method of claim 16, comprising the navigation system registering the surgical plan data to the localizer coordinate system by combining:
a first transform defining a relationship between the physical bone and the bone tracker; and
a second transform defining a relationship between the bone tracker and the localizer.

19. The method of claim 16, wherein the HMD further comprises a video camera and the navigation system further comprises a registration device including a plurality of registration markers that are detectable by the localizer and by the video camera of the HMD, the method further comprising the navigation system:
registering the HMD to the localizer coordinate system by combining a first transform defining a relationship between the HMD and the registration device and a second transform a relationship between the registration device and the localizer.

20. The method of claim 16, wherein the navigation system comprises an HMD tracker coupled to the HMD, the method further comprising the navigation system registering the HMD to the localizer coordinate system through detection of a pose of the HMD tracker.

21. The method of claim 16, wherein the HMD further comprises a video camera, the method comprising the HMD controller aligning and combining the computer-generated imagery with real-world video of the physical bone captured by the video camera of the HMD.

22. The method of claim 16, wherein the surgical plan data further comprises a size of the implant and/or a placement of the implant, the method comprising the HMD controller further providing, on the display, computer-generated imagery representative of the surgical plan data, including the size of the implant and/or the placement of the implant.

23. The method of claim 16, further comprising a surgical tool that is configured to remove the material from the physical bone in preparation for receiving the implant, and wherein the navigation system further includes a tool tracker coupled to the surgical tool, the method further comprising:
the navigation system monitoring the tool tracker to track poses of the surgical tool in the localizer coordinate system; and
the HMD controller further providing, on the display, computer-generated imagery representative of the surgical tool relative to the computer-generated imagery including the virtual model of the physical bone and the cut volume data.

24. The method of claim 16, further comprising a manipulator comprising a base and a robotic arm extending from the base, wherein the robotic arm is configured to support and move a surgical tool that is configured to remove the material from the physical bone in preparation for receiving the implant, and wherein the navigation system further includes a tracker coupled to the manipulator, the method further comprising:
the navigation system monitoring the tracker to track a pose of the surgical tool in the localizer coordinate system; and
the HMD controller further providing, on the display, computer-generated imagery representative of the surgical tool relative to the computer-generated imagery including the virtual model of the physical bone and the cut volume data.

25. The method of claim 24, wherein the surgical plan data further comprises a tool path along which the manipulator moves, or will move, the surgical tool to remove the material from the physical bone in preparation for receiving the implant, the method further comprising:
the HMD controller further providing, on the display, computer-generated imagery representative of the tool path relative to the computer-generated imagery including the virtual model of the physical bone and the cut volume data.

26. The method of claim 16, wherein the HMD further comprises a sensor configured to recognize gesture commands from the wearer of the HMD, the method further comprising the HMD controller detecting the gesture commands to enable modifying the surgical plan data.

27. A head-mounted device (HMD) for use with a navigation system, the navigation system including a localizer and a bone tracker coupled to a physical bone of a patient, wherein the localizer comprises a localizer coordinate system and is configured to monitor the bone tracker to track a pose of the physical bone in the localizer coordinate system, the HMD comprising:
an HMD controller; and
a display that is configured to be located in front of eyes of a wearer of the HMD; and
wherein the HMD controller is configured to:
receive, from the navigation system, surgical plan data related to the physical bone, wherein the surgical plan data comprises a virtual model of the physical bone, cut volume data defining material to be removed from the physical bone in preparation for receiving an implant, and a textual note previously created by a surgeon during surgical planning related to the physical bone, wherein the textual note is associated with a particular surgical step related to the physical bone;
register to the localizer coordinate system;
provide, on the display, computer-generated imagery representative of the surgical plan data, including the virtual model of the physical bone and the cut volume data;
align and combine the computer-generated imagery with a real-world view of the physical bone; and
automatically present, on the display, the textual note at the time of the particular surgical step with which the textual note is associated.

28. The HMD of claim 27, further comprising a video camera, and wherein the HMD controller is configured to register to the localizer coordinate system through detection, with the video camera, of registration markers of a registration device, wherein the registration markers are also detectable by the localizer.

29. The HMD of claim 27, further comprising an HMD tracker coupled to the HMD, wherein the HMD tracker is configured to be detected by the localizer and to enable the HMD controller to register to the localizer coordinate system.

30. The HMD of claim 27, wherein the HMD further comprises a video camera, and wherein the real-world view is further defined as a real-world video captured by the video camera of the HMD.

31. The HMD of claim 27, wherein:
the surgical plan data further comprises a size of the implant and/or a placement of the implant; and
the HMD controller is configured to further provide, on the display, computer-generated imagery representative of the surgical plan data, including the size of the implant and/or the placement of the implant.

32. The HMD of claim 27, wherein the HMD controller is configured to provide, on the display, computer-generated imagery representative of a surgical tool relative to the computer-generated imagery including the virtual model of the physical bone and the cut volume data.

33. The HMD of claim 27, wherein the cut volume data further comprises a virtual cutting boundary that defines the material to be removed from the physical bone.

34. The HMD of claim 27, wherein the HMD controller is configured to further provide, on the display, computer-generated imagery representative of a tool path relative to the computer-generated imagery including the virtual model of the physical bone and the cut volume data.

35. The HMD of claim 27, further comprising a sensor configured to recognize gesture commands from the wearer, and wherein the HMD controller is configured to detect the gesture commands to enable modification to the surgical plan data.

36. The HMD of claim 27, wherein the display is further defined as an organic light-emitting diode display.

37. A head-mounted device (HMD) for providing surgical guidance related to a physical bone of a patient, the HMD comprising:
an HMD controller;
a video camera; and
a display that is configured to be located in front of eyes of a wearer of the HMD; and
wherein the HMD controller is configured to:
receive surgical plan data related to the physical bone, wherein the surgical plan data comprises a virtual model of the physical bone, cut volume data defining material to be removed from the physical bone in preparation for receiving an implant, and a textual note previously created by a surgeon during surgical planning related to the physical bone, wherein the textual note is associated with a particular surgical step related to the physical bone;
register to the physical bone;
provide, on the display, computer-generated imagery representative of the surgical plan data, including the virtual model of the physical bone and the cut volume data;
align and combine the computer-generated imagery with a real-world video of the physical bone captured by the video camera; and
automatically present, on the display, the textual note at the time of the particular surgical step with which the textual note is associated.

* * * * *